(12) United States Patent
VanNieuwenhze et al.

(10) Patent No.: US 11,168,077 B2
(45) Date of Patent: Nov. 9, 2021

(54) MOLECULAR ROTOR-BASED D-AMINO ACIDS AS TOOLS FOR IMAGING PEPTIDOGLYCAN BIOSYNTHESIS

(71) Applicant: Indiana University Research and Technology Corporation, Indianapolis, IN (US)

(72) Inventors: Michael VanNieuwenhze, Bloomington, IN (US); Yves Brun, Montreal (CA); Erkin Kuru, Jamaica Plain, MA (US); Edward Hall, Hanover, IN (US)

(73) Assignee: Indiana University Research and Technology Corporation, Indianapolis, IN (US)

( * ) Notice: Subject to any disclaimer, the term of this patent is extended or adjusted under 35 U.S.C. 154(b) by 0 days.

(21) Appl. No.: 16/967,874

(22) PCT Filed: Feb. 7, 2019

(86) PCT No.: PCT/US2019/017132
§ 371 (c)(1),
(2) Date: Aug. 6, 2020

(87) PCT Pub. No.: WO2019/157233
PCT Pub. Date: Aug. 15, 2019

(65) Prior Publication Data
US 2021/0047308 A1    Feb. 18, 2021

Related U.S. Application Data

(60) Provisional application No. 62/793,734, filed on Jan. 17, 2019, provisional application No. 62/627,728, filed on Feb. 7, 2018.

(51) Int. Cl.
*C07D 409/04* (2006.01)

(52) U.S. Cl.
CPC ................... *C07D 409/04* (2013.01)

(58) Field of Classification Search
CPC ..................................... C07D 409/04
See application file for complete search history.

(56) References Cited

FOREIGN PATENT DOCUMENTS

| WO | 2013159078 | 10/2013 |
| WO | 2015038764 | 3/2015 |

OTHER PUBLICATIONS

International Search Report issued by the European Patent Office, dated Apr. 30, 2019, for International Patent Application No. PCT/US2019/017132; 4 pages.

Felipe Cava, et al., "Distinct pathways for modification of the bacterial cell wall by non-canonical D-amino acids", The EMBO Journal, Aug. 17, 2011; 12 pages.

Erkin Kuru, et al., "Synthesis of fluorescent D-amino acids and their use for probing peptidoglycan synthesis and bacterial growth in situ", Nature Protocols, vol. 10, No. 1, Dec. 4, 2014; 41 pages.

Hsu Yen-Pang, et al. "Fluorogenic d-amino acids enable real-time monitoring of peptidoglycan biosnythesis and high-throughput transpeptidation assays", Nature Chemistry, Nature Publishing Group UK, London, vol. 11, No. 4, Feb. 25, 2019; 15 pages.

Written Opinion issued by the European Patent Office, dated Apr. 30, 2019, for International Patent Application No. PCT/US2019/017132; 6 pages.

*Primary Examiner* — Rebecca L Anderson
(74) *Attorney, Agent, or Firm* — Faegre Drinker Biddle & Reath LLP

(57) ABSTRACT

Disclosed herein are compositions for assessing peptidoglycan (PG) biosynthesis in bacteria using modified D-amino acids covalently attached to a molecular rotor and visualizing the labeled PG in bacteria based upon the enhanced fluorescence of the molecular rotor incorporated in the PG. The resultant, labeled peptidoglycan structures are amenable for identification by microscopic visualization, flow cytometry or other suitable methods.

1 Claim, 24 Drawing Sheets

(i)

(ii)

MOLECULAR ROTOR-BASED D-AMINO ACIDS AS TOOLS FOR IMAGING PEPTIDOGLYCAN BIOSYNTHESIS

CROSS-REFERENCE TO RELATED APPLICATIONS

This application claims benefit of priority under 35 U.S.C. 119 to U.S. Provisional Patent Application Ser. No. 62/627,728, filed Feb. 7, 2018 and U.S. Provisional Patent Application Ser. No. 62/793,734, filed Jan. 17, 2019, each of which is entitled "MOLECULAR ROTOR-BASED D-AMINO ACIDS AS TOOLS FOR IMAGING PEPTIDO-GLYCAN BIOSYNTHESIS," the contents of each are herein incorporated by reference in their entirety.

STATEMENT REGARDING FEDERALLY SPONSORED RESEARCH OR DEVELOPMENT

This invention was made with government support under A1059327 and GM051986 awarded by the National Institutes of Health. The Government has certain rights in the invention.

1. TECHNICAL FIELD

The present disclosure relates to molecular rotor-based D-amino acids for incorporation into bacterial cell wall peptidoglycans and their use in post-labeling methods to visualize peptidoglycan biosynthesis by light microscopy.

2. DESCRIPTION OF RELATED ART

Bacterial growth is controlled by the domain-specific peptidoglycan (PG) cell wall, a rigid and essential structure composed of glycan strands cross-linked by D-amino acid (DAA)-containing short peptides, whose biosynthesis machinery is a target for antibiotics.

Despite the importance of PG, knowledge of its dynamics has been severely hampered by lack of a strategy for direct imaging of sites of PG biosynthesis in live cells. Significant limitations of current labeling methods, such as toxic effects and poor membrane permeability of the probes, have limited their applicability to only a small set of bacterial species. Moreover, these methods are labor-intensive and their sensitivity suffers from their indirect and multiple-step nature.

Methods relying on fluorescently labeled antibiotics to study bacterial cell wall synthesis and to discover new antibiotics to which bacteria remain susceptible have had a profound impact on the field. The current methods, however, have at least two inherent limitations. First, antibiotic concentration needs to be carefully controlled to avoid damage to the cell. Second, because these agents bind to specific sites on cell surfaces, they only will appear at sites of active PG biosynthesis.

The present inventors have disclosed previously a class of fluorescently-modified D-amino acids (FDAAs) that have enabled the visualization of peptidoglycan synthesis dynamics in live bacterial cells. See International Patent Application No. PCT/US13/37504, filed Apr. 21, 2013, to INDIANA UNIVERSITY RESEARCH & TECHNOLOGY CORPORATION, entitled COMPOSITIONS FOR IN SITU LABELING OF BACTERIAL CELL WALLS WITH FLUOROPHORES AND METHODS OF USE THEREOF. While having found broad utility within the field that studies peptidoglycan biosynthesis, this approach is limited by: 1) the requirement of a washing step, prior to imaging, in order to minimize background fluorescence, and 2) the requirement for fixing of cells, in order to limit cell growth during sample preparation for imaging.

The inventors have developed a new class of fluorescent probes, namely FMR-DAAs, based upon fluorescent molecular rotors, that fluoresce only upon incorporation into peptidoglycan and, as a result, that do not require sample washing and fixing.

BRIEF SUMMARY

In a first aspect, a modified amino acid is provided, wherein the modified amino acid includes a D-amino acid covalently attached to either structure (I) or structure (II):

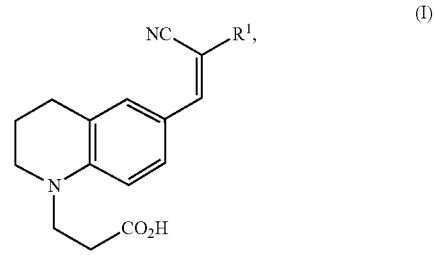

(I)

wherein $R^1$ is selected from —CN and —CO$_2$H; and

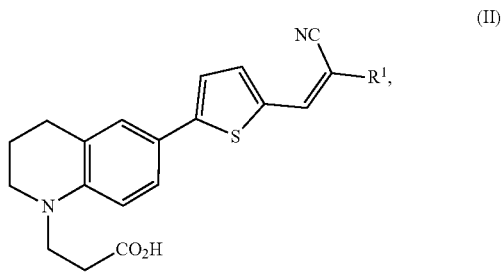

(II)

wherein $R^1$ is selected from —CN, —CO$_2$H and SO$_3$H.

In a second aspect, a muramylpentapeptide precursor unit is disclosed that includes an N-acetyl muramic acid (NAM) moiety having a stem peptide of three to five amino acids. One or more of the amino acids in the stem peptide includes a modified amino acid that includes a D-amino acid covalently attached to either structure (I) or (II).

In a third aspect, a peptidoglycan unit is disclosed that includes a muramylpentapeptide precursor unit as described above in the second aspect that is covalently linked to an N-acetyl glucosamine (NAG) moiety.

In a fourth aspect, a live bacterial organism is provided. The live bacterial organism includes a bacterium having a modified cell wall comprising modified peptidoglycan containing at least one modified D-amino acid covalently attached to either structure (I) or (II)

In a fifth aspect, a method of assessing bacterial cell wall synthesis in real time is described. The method includes the step of providing live bacteria with a first amount of at least one modified amino acid comprising a D-amino acid covalently attached to either structure (I) or (II) under conditions sufficient for bacterial cell wall synthesis, wherein the bacteria covalently incorporate the at least one modified amino acid into a stem peptide of peptidoglycan of the bacterial cell wall.

In a sixth aspect, a method of screening for a putative cell wall-acting agent is disclosed. The method includes the step of co-contacting bacteria with an effective amount of an agent and an amount of at least one modified amino acid comprising a D-amino acid covalently attached to either structure (I) or (II) under conditions sufficient to permit ongoing peptidoglycan biosynthesis in a bacterial cell wall, wherein the agent comprises a cell wall-acting agent if the agent interferes with ongoing peptidoglycan biosynthesis in the bacterial cell wall.

In a seventh aspect, a method of screening for a putative cell wall-disrupting agent is disclosed. The method includes the step of contacting modified bacteria with an amount of an agent. The agent is a cell wall-disrupting agent if the agent weakens integrity of peptidoglycan in an existing bacterial cell wall. In this method, the modified bacteria have a modified cell wall containing modified peptidoglycan having at least one stem peptide containing at least one modified amino acid comprising a D-amino acid covalently attached to either structure (I) or (II).

In an eighth aspect, a method of identifying bacteria is disclosed. The method includes three steps. The first step includes contacting live bacteria with an amount of at least one modified amino acid comprising a D-amino acid covalently attached to either structure (I) or (II) under conditions sufficient for ongoing bacterial cell wall synthesis. The bacteria covalently incorporate into peptidoglycan of a bacterial cell wall the at least one modified amino acid. Each of the least one modified amino acid comprises a distinct bioorthogonal tag. The second step includes visualizing the label to determine an incorporation pattern of the at least one modified amino acid wherein the incorporation pattern identifies the bacteria.

In a ninth aspect, a kit for incorporating modified amino acids into live bacteria is disclosed. The kit includes at least one modified amino acid comprising a D-amino acid covalently attached to either structure (I) or (II) and a positive bacterial control. The kit can include an optional negative bacterial control. The positive bacterial control has at least one modified amino acid comprising a D-amino acid covalently attached to either structure (I) or (II) incorporated into a stem peptide of peptidoglycan of the bacterial cell wall. The optional negative bacterial control, if included, does not have the modified amino acid comprising a D-amino acid attached to either structure (I) or (II) incorporated into a stem peptide of peptidoglycan of the bacterial cell wall.

In a tenth aspect, a method of wash-free labeling of bacterial cell wall peptides is provided. The method includes several steps. The first step includes contacting live bacteria with an amount of at least one modified amino acid of the first aspect under conditions sufficient for ongoing bacterial cell wall synthesis. The second step includes covalently incorporating into a peptide of a bacterial cell wall the at least one modified amino acid to form a covalent bond of the at least one modified amino acid with the peptide of the cell wall. The covalent modification of the peptide of the cell wall with the at least one modified amino acid results in producing a detectable label signal without requiring washing the bacterial cells following contacting the bacterial cells with the at least one modified amino acid.

These and other features, objects and advantages of the present invention will become better understood from the description that follows. In the description, reference is made to the accompanying drawings, which form a part hereof and in which there is shown by way of illustration, not limitation, embodiments of the invention.

BRIEF DESCRIPTION OF THE DRAWINGS

The features, objects and advantages other than those set forth above will become more readily apparent when consideration is given to the detailed description below. Such detailed description makes reference to the following drawings.

PG with FMR-probe-D-Lys conjugates having the FMR probe moiety of formula (II), wherein $R^1$ consists of a —CN moiety (panel (iii)).

Figure 6:
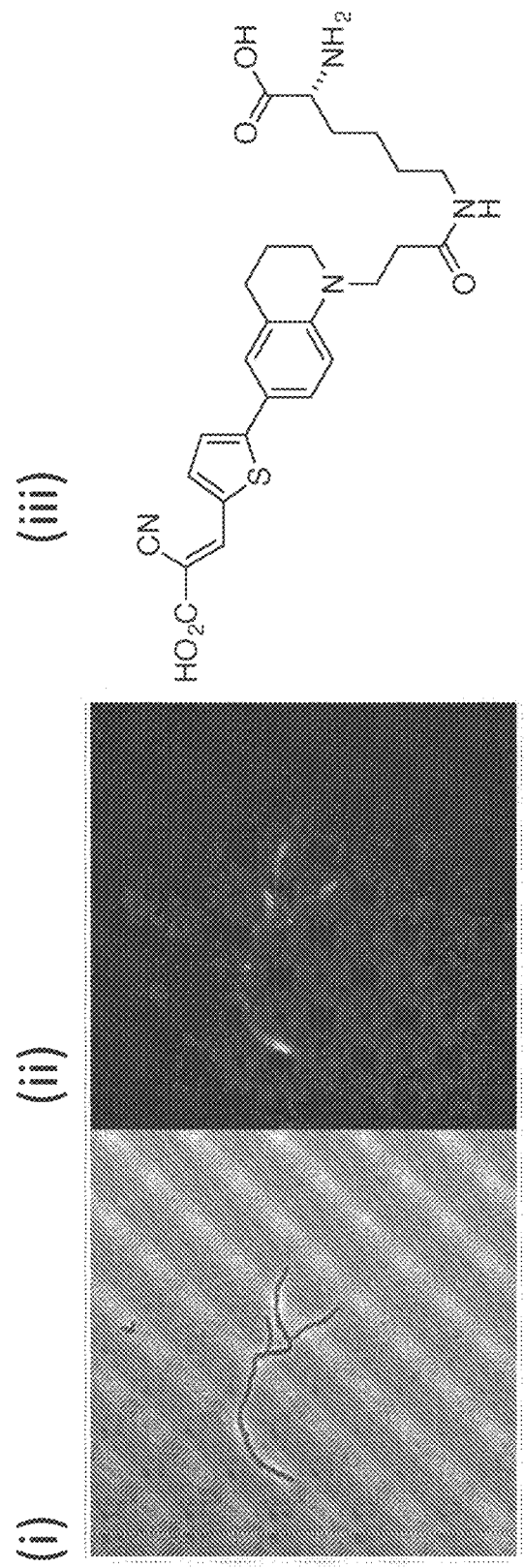

FIG. 6 depicts exemplary labeling (phase contrast in panel (i) and fluorescence contrast in panel (ii)) of *S. venezuelae* PG with FMR-probe-D-Lys conjugates having the FMR probe moiety of formula (II), wherein $R^1$ consists of a —$CO_2H$ moiety (panel (iii)).

Figure 7:
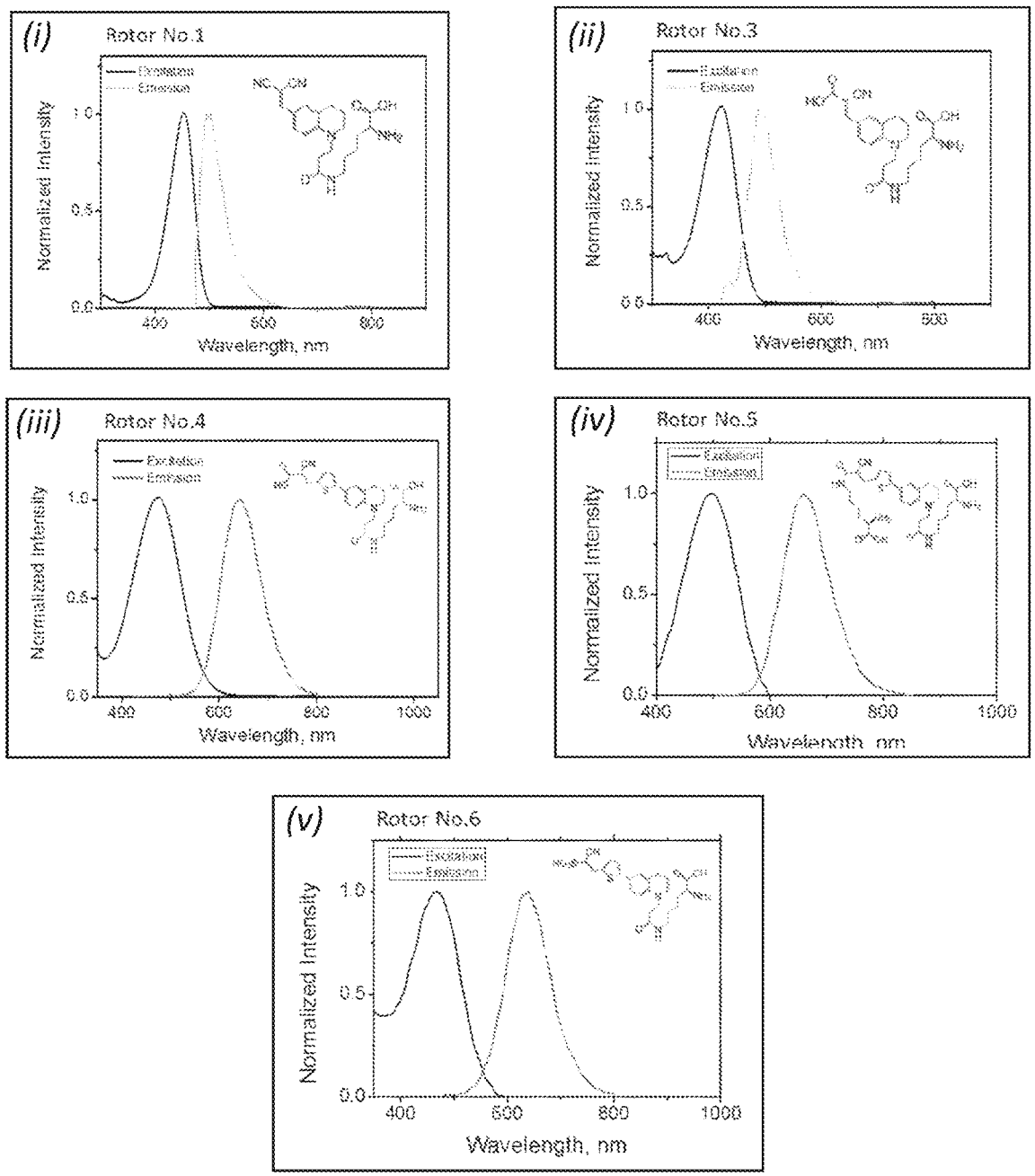

FIG. 7 depicts exemplary spectral plots for first generation and third-sixth generation molecular rotor designs (panels (i)-(v)).

Figure 8:
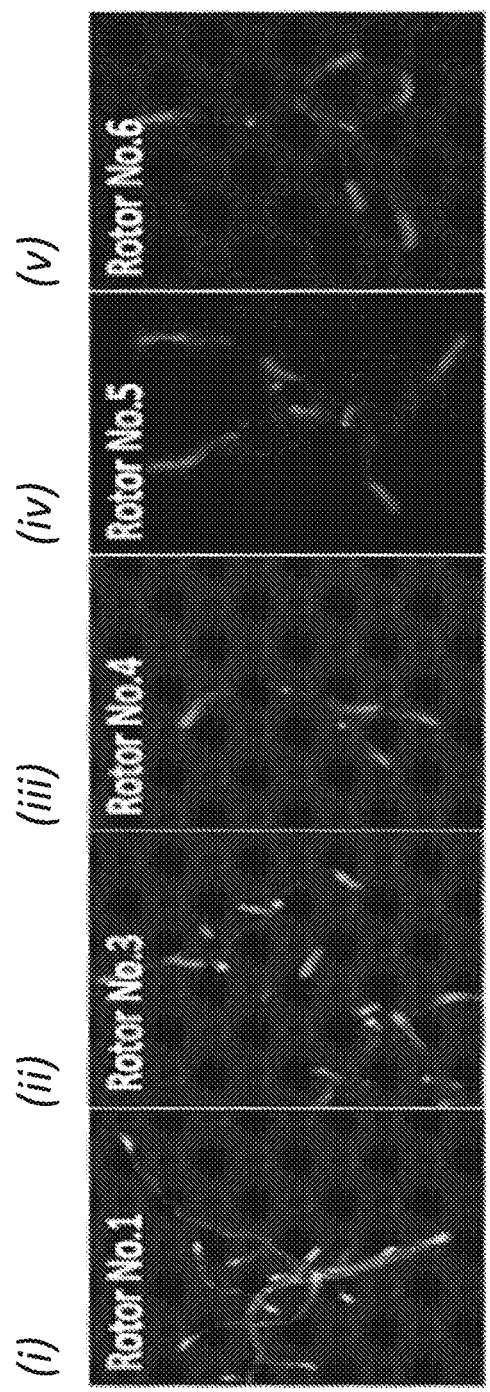

FIG. 8 illustrates exemplary results of labeling the *Streptomysis venezuulae* cells with first generation and third-sixth generation molecular rotor designs (panels (i)-(v)).

Figure 9:
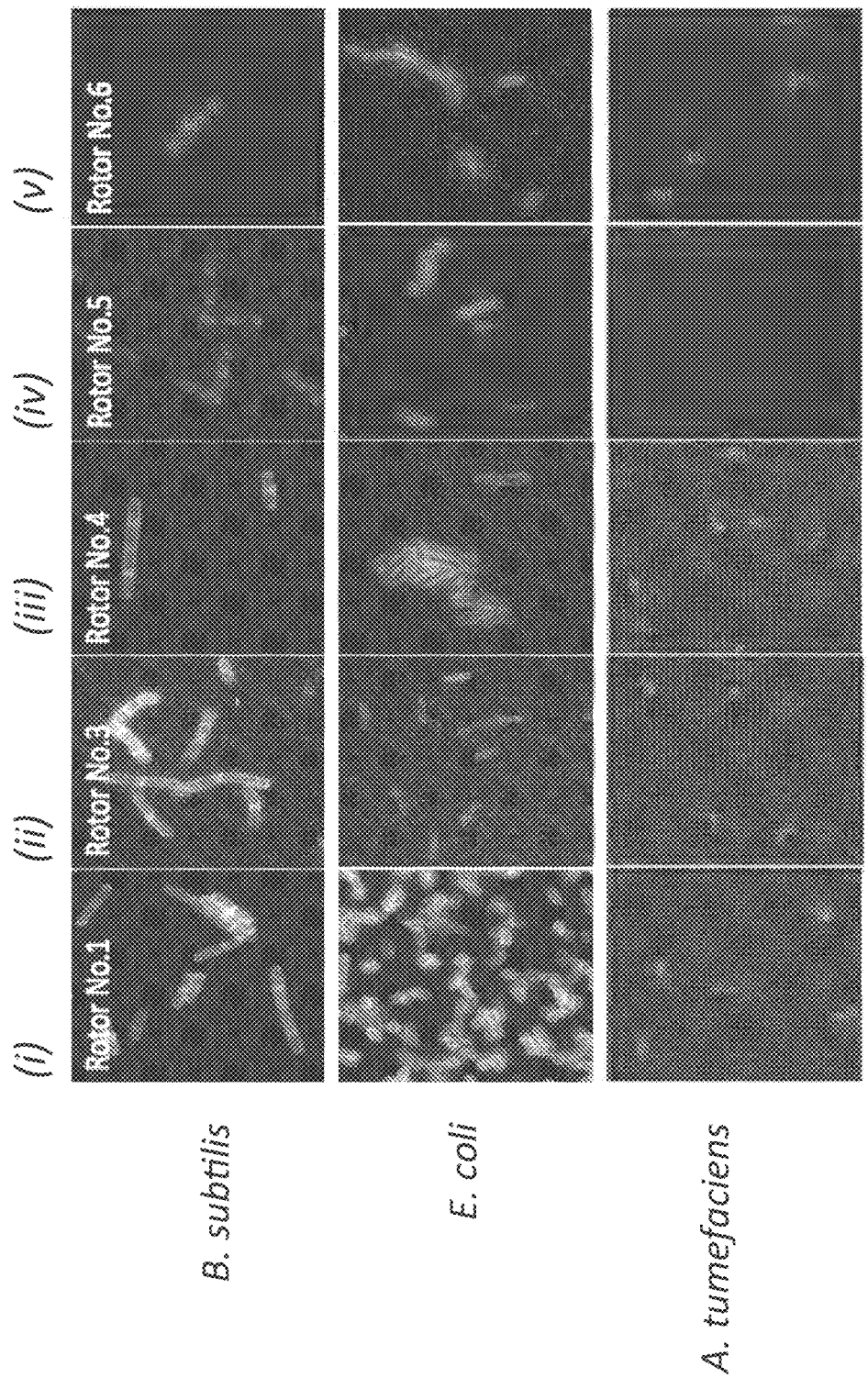

FIG. 9 illustrates exemplary results of labeling *B. subtilis*, *E. coli* and *A. tumefaciens* cells with first generation and third-sixth generation molecular rotor designs (panel sets (i)-(v)).

Figure 10:
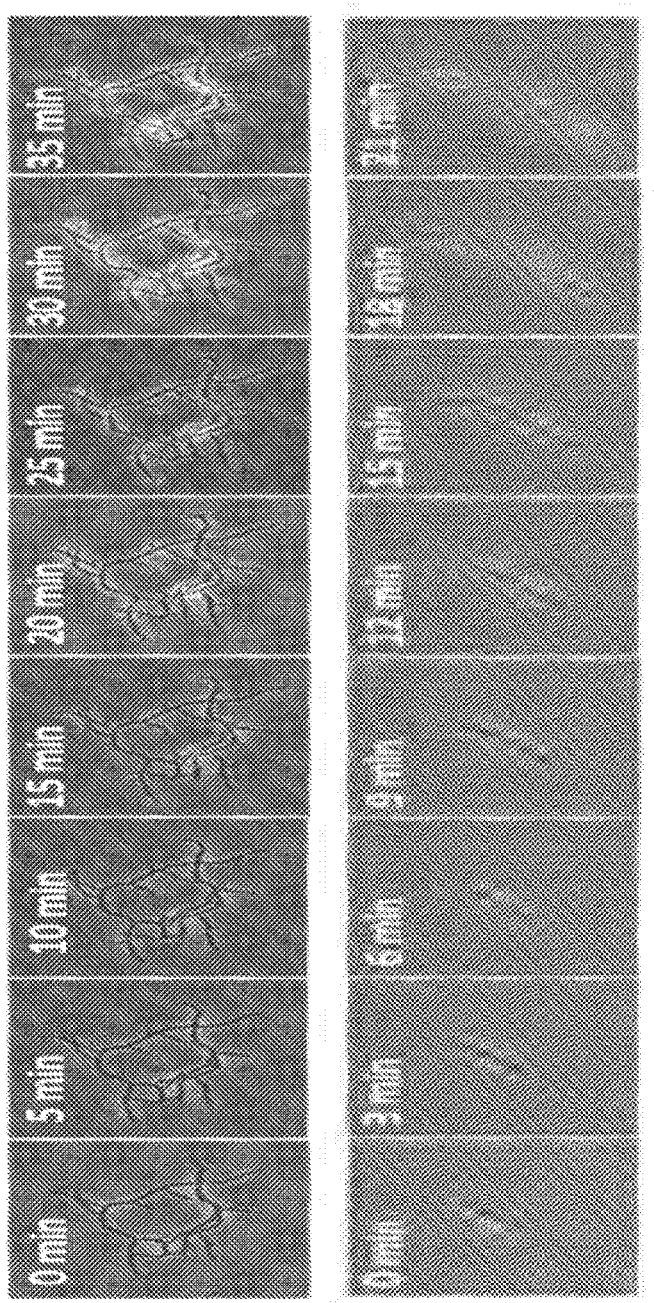

FIG. 10 illustrates exemplary results of labeling *S. venezuelae* and *B. subtilis* cells with fourth generation molecular rotor design over time (0-35 min).

Figure 11:
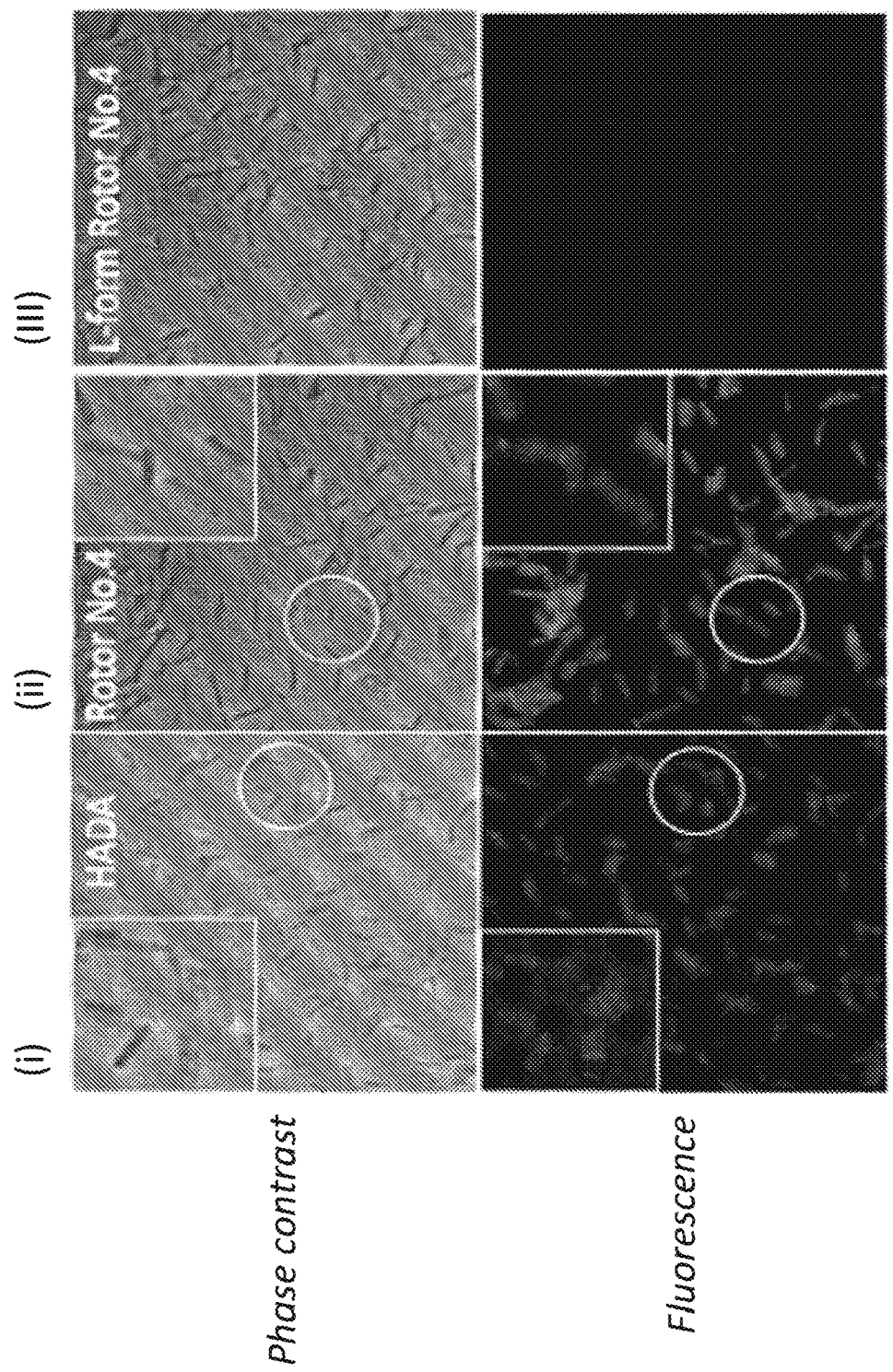

FIG. 11 illustrates exemplary results of labeling *B. subtilis* cells with HADA (panel set (i)), D-form of fourth generation molecular rotor design (panel set (ii)) and L-form of fourth generation molecular rotor design (panel set (iii)), wherein phase contrast imaging is illustrated for the upper images and fluorescence imaging is illustrated for the lower images.

Figure 12A:
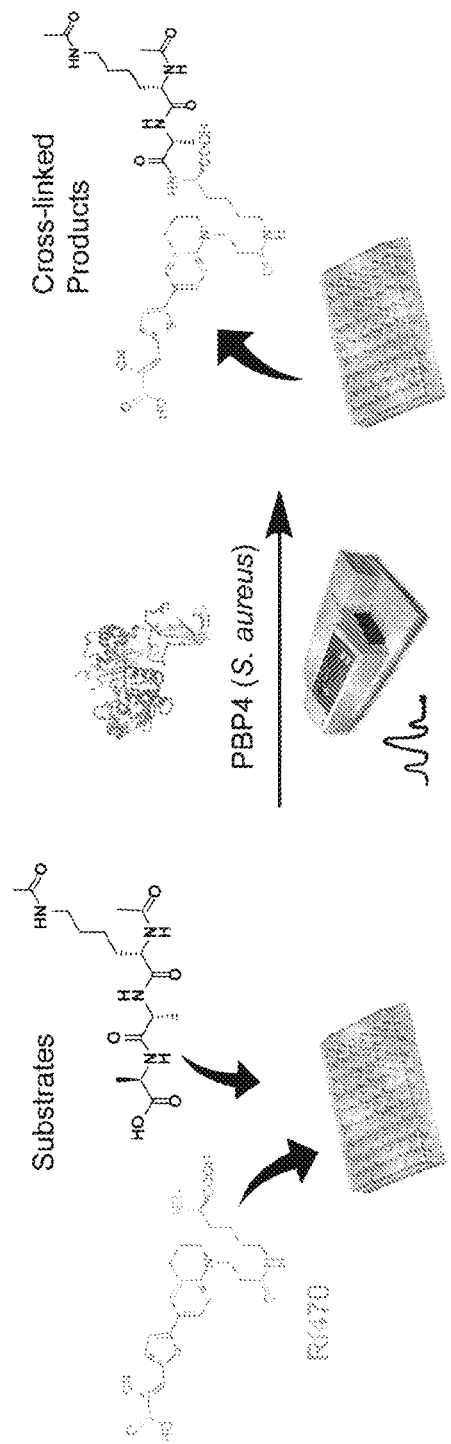

FIG. 12A depicts an exemplary scheme for the assay procedure for in vitro D,D-transpeptidation assays using Rf470 and isolated *S. aureus* PBP4.

Figure 12B:
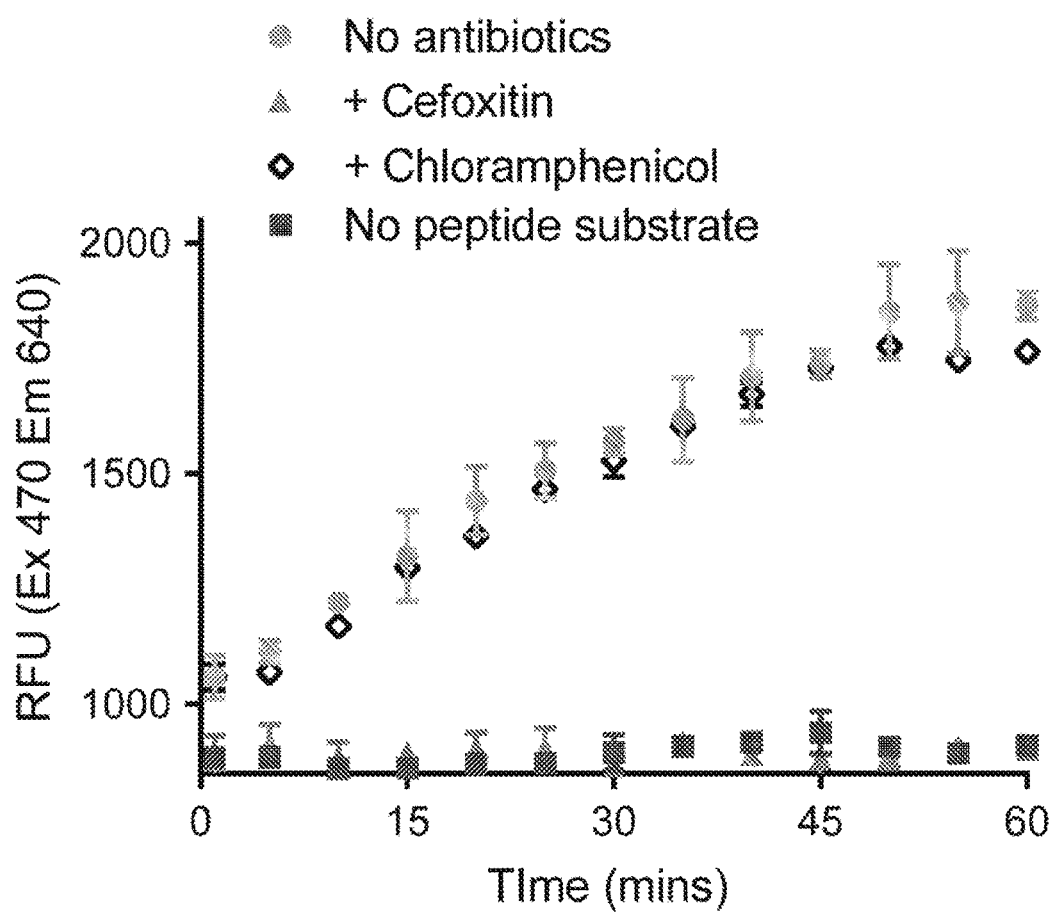

FIG. 12B depicts real-time measurements of Rf470 fluorescence intensity.

Figure 12C:
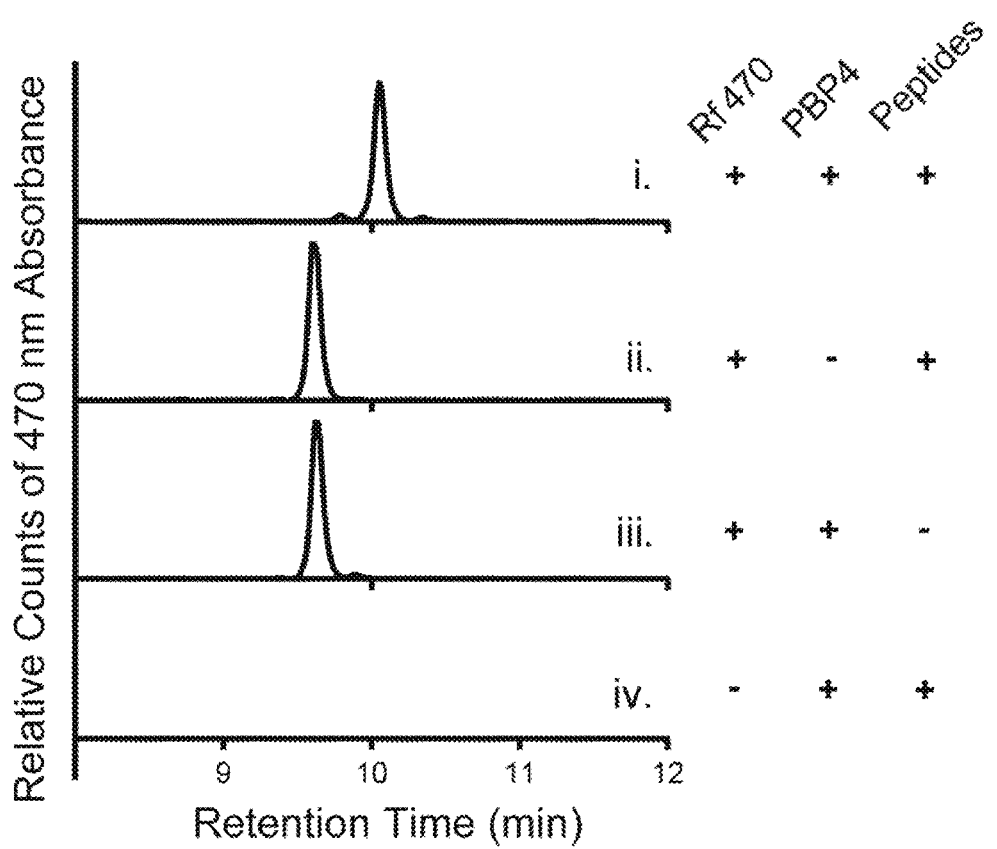

FIG. 12C depicts HPLC analysis of products from the D,D-transpeptidation assay.

Figure 12D:

FIG. 12D depicts HRMS analysis of the products from the assay.

Figure 12E:
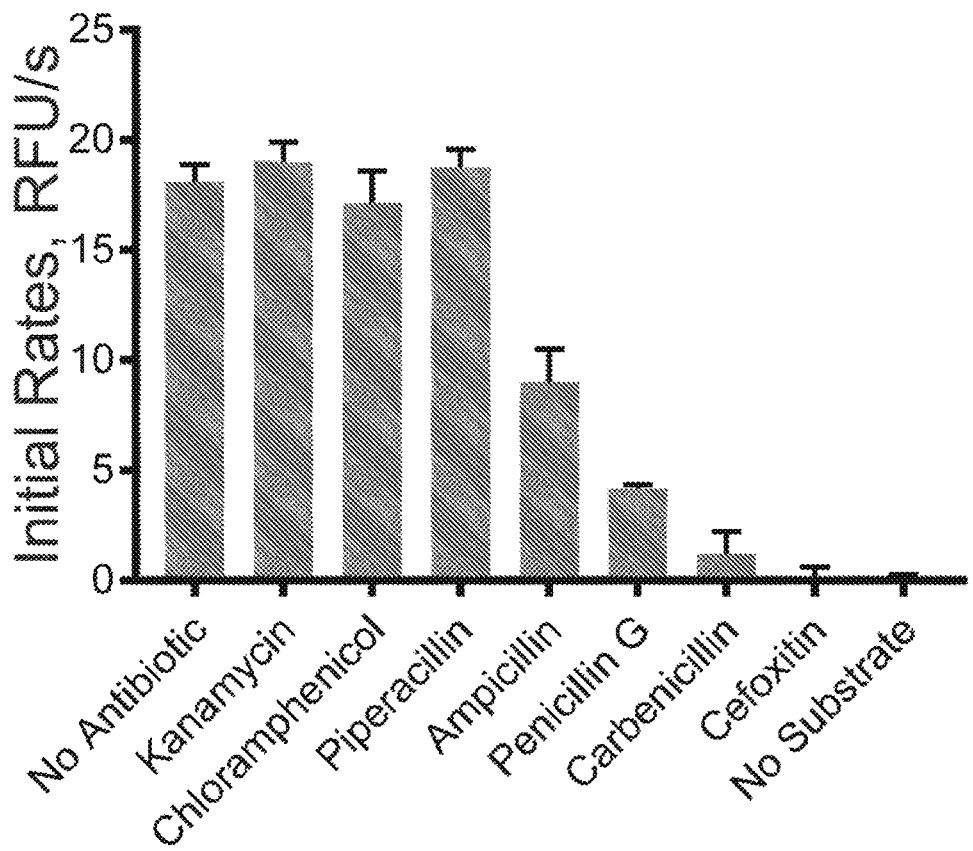

FIG. 12E depicts screening of antibiotic effect on *S. aureus* PBP4 activity. Kanamycin and Chloramphenicol: ribosome activity inhibitors; Piperacillin, Ampicillin, Penicillin G, Carbenicillin and Cefoxitin are β-lactam antibiotics. A 1:10 ratio of antibiotics to the substrate was used.

Figure 12F:
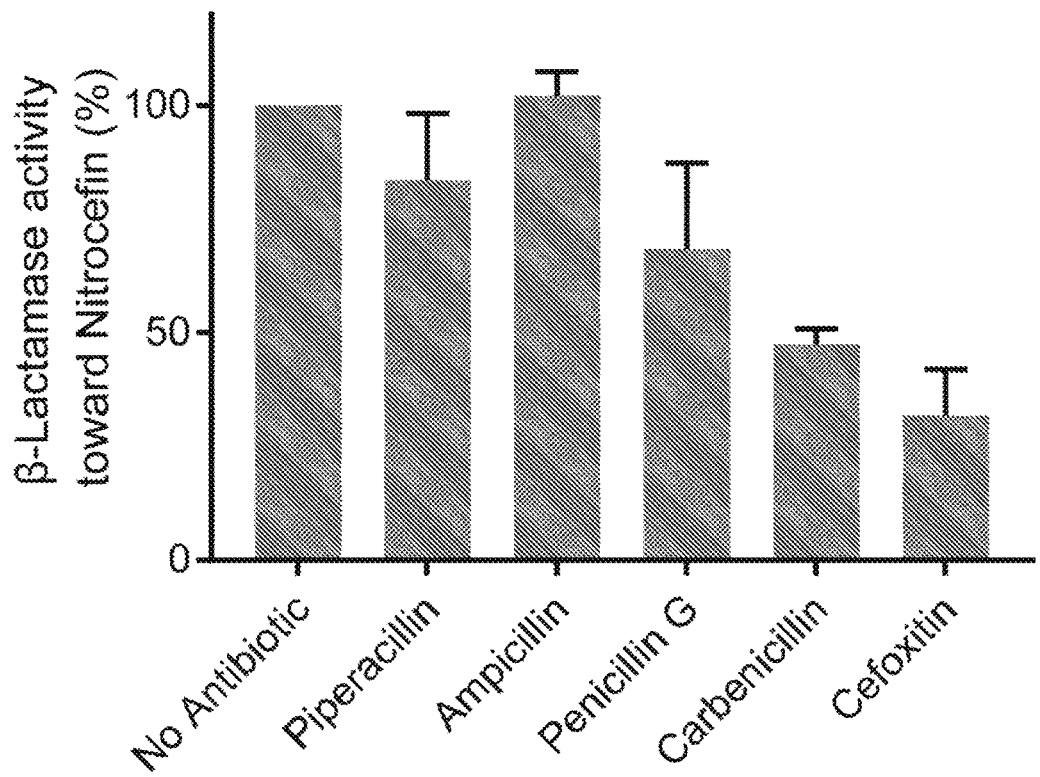

FIG. 12F depicts β-lactamase activity of *S. aureus* PBP4 in the presence of antibiotics. Nitrocefin degradation by PBP4 results in an increase of absorbance at 500 nm, which is used to measure β-lactamase activity. Low activity stands for a strong inhibition effect of the antibiotics toward PBP4, and vice versa. Values are normalized to the "no antibiotic" sample.

While the present invention is amenable to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the embodiments above and the claims below. Reference should therefore be made to the embodiments and claims herein for interpreting the scope of the invention.

DETAILED DESCRIPTION

The compositions and methods now will be described more fully hereinafter with reference to the accompanying drawings, in which some, but not all permutations and variations of embodiments of the invention are shown. Indeed, the invention may be embodied in many different forms and should not be construed as limited to the embodiments set forth herein. These embodiments are provided in sufficient written detail to describe and enable one skilled in the art to make and use the invention, along with disclosure of the best mode for practicing the invention, as defined by the claims and equivalents thereof.

Likewise, many modifications and other embodiments of the compositions and methods described herein will come to mind to one of skill in the art to which the invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the invention pertains. Although any methods and materials similar to or equivalent to those described herein can be used in the practice or testing of the present invention, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one."

As used herein, "about" means within a statistically meaningful range of a value or values such as a stated concentration, length, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

As used herein, the term "molecular rotor" refers to a member of a group of fluorescent molecules with an intramolecular charge transfer (ICT) mechanism, which undergoes a twisting motion in the excited state. This family of fluorophores is often known as twisted intramolecular charge transfer (TICT) complexes. After photon absorption, a molecular rotor can return to the ground state either from the locally excited (LE) state or from the twisted state. The energy gaps between the LE and twisted states to the ground state are very different, and the deexcitation from the twisted state has either a red-shifted emission wavelength or no emission at all. One feature of molecular rotors is the dependency of the twisted-state deexcitation rate on the local environment, namely on the solvent's microviscosity and polarity.

Overview

Previous efforts to label PG in live bacteria principally have relied upon cell wall-active antibiotics (e.g., vancomycin, ramoplanin) modified with fluorophores or cell wall precursors/substrates covalently modified with fluorescent reporter groups. The compositions and methods described herein, however, take advantage of mechanisms for incorporating labeled DAAs into the stem peptides displayed on a bacterial cell wall surface.

The work described herein demonstrates how to make derivatized fluorescent molecular rotor probe-DAA conjugates ("FMR-probe-DDA conjugates", or FMR-DAAs) having a suitable label, such that such derivatized compounds can be visualized in live cells by fluorescence microscopy, for example, following the incorporation of the derivatized compounds into PG and thus the cell wall. In the range of physiologically relevant concentrations, the incorporated FMR-DAAs do not appear to be toxic to bacteria. Unlike previous methods that employ covalently modified cell wall precursors, the methods described herein do not appear to adversely affect cell morphology. In addition, the methods described herein enable real-time experiments that cannot be easily executed in the presence of fluorescently modified cell wall active drugs. Because the disclosed derivatized compounds have low or minimal toxicity to live cells, they are ideal markers to evaluate and screen microbiostatic or microbiotoxic compounds that do adversely affect microorganism growth and viability, such as studies directed to development of novel antibiotics.

Studies disclosed herein demonstrate that the compositions and methods are applicable to a wide array of Gram-positive and Gram-negative bacteria and provides significant utility for probing PG biosynthesis, cell wall morphogenesis and the response of the PG biosynthetic machinery to cell wall-active agents and/or cell wall-disrupting agents. The present disclosure therefore provides compositions and methods for studying bacterial cell wall PG biosynthesis and for discovering bacterial cell wall acting and/or cell wall-disrupting agents.

Compositions

Molecular Rotor-Based Amino Acids for Real-Time Detection of PG Synthesis

Current FDAAs require washing to eliminate the background from unincorporated probes, thereby decreasing the temporal resolution of experiments. Moreover, this prevents observation of FDAA incorporation in real time, which also limits the use of FDAAs as a diagnostic tool of bacterial infections in medical applications. This problem can be addressed via fluorogenic probes that "turn-on" immediately upon incorporation into PG. Several common strategies for fluorogenic probe activation will likely not work for PG labeling for the following reasons. First, pH and polarity do not differ significantly in the PG environment compared to the growth medium. Second, addition of enzymes, metal ions, or small molecules to activate the fluorophore will not discriminate incorporated from non-incorporated probes. Third, the D-amino acid center does not quench probe fluorescence in solution, preventing a turn-on effect upon incorporation. Finally, known fluorogenic bioorthogonal probe partners still require a washing step of the excess reporter.

To overcome these strategic shortcomings, one can use fluorescent molecular rotor-based probes (FMR-probes) that take advantage of the restrictive steric environment of the PG. FMR-probes are non-fluorescent (or very weakly so) when free in solution; however, restriction of key bond rotation prevents non-radiative relaxation of fluorophore-excited states leading to vast increases in fluorescence. Indeed, this class of probes has found success in the study of viscosity in cellular microenvironments, DNA intercalating agents, and modern applications as fluoromodules. See for examples, Haidekker, M. A. and E. A. Theodorakis, "Environment-sensitive behavior of fluorescent molecular rotors," *J. Biol. Eng.* 4:11 (2010); Köhler, O., D. V. Jarikote, and O. Seitz, "Forced Intercalation Probes (FIT Probes): Thiazole Orange as a Fluorescent Base in Peptide Nucleic Acids for Homogeneous Single Nucleotide-Polymorphism Detection," *Chem Bio Chem* 6:69-77 (2005); and Özhalici-Ünal, H. et al., "A Rainbow of Fluoromodules: A Promiscuous scFv Protein Binds to and Activates a Diverse Set of Fluorogenic Cyanine Dyes," *J. Am. Chem. Soc.* 130:12620-12621 (2008).

In one aspect, an FMR-probe having the structure of formula (I) is provided:

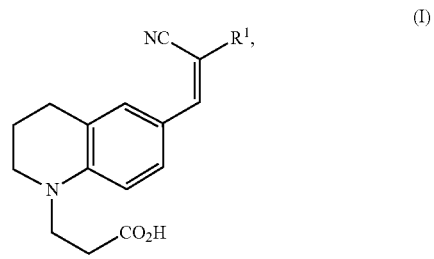

wherein $R^1$ is selected from —CN and —$CO_2H$.

The presence of the carboxylic acid provides a site for covalent coupling of the FMR-probe to an available amino group on a D-amino acid backbone, such as D-amino-Ala or D-Lys. As FMR-probes having $R^1$ consist of a cyano moiety provide slight affinity for bacterial membranes, result in low levels of nonspecific labeling and some instability of the α,β-unsaturated malononitrile moiety under typical experimental conditions, such FMR-probes are less preferred for use. In such cases, FMR-probes having $R^1$ consisting of a carboxylic acid can prevent non-specific membrane binding and increase stability of the probe.

Figure 3A:
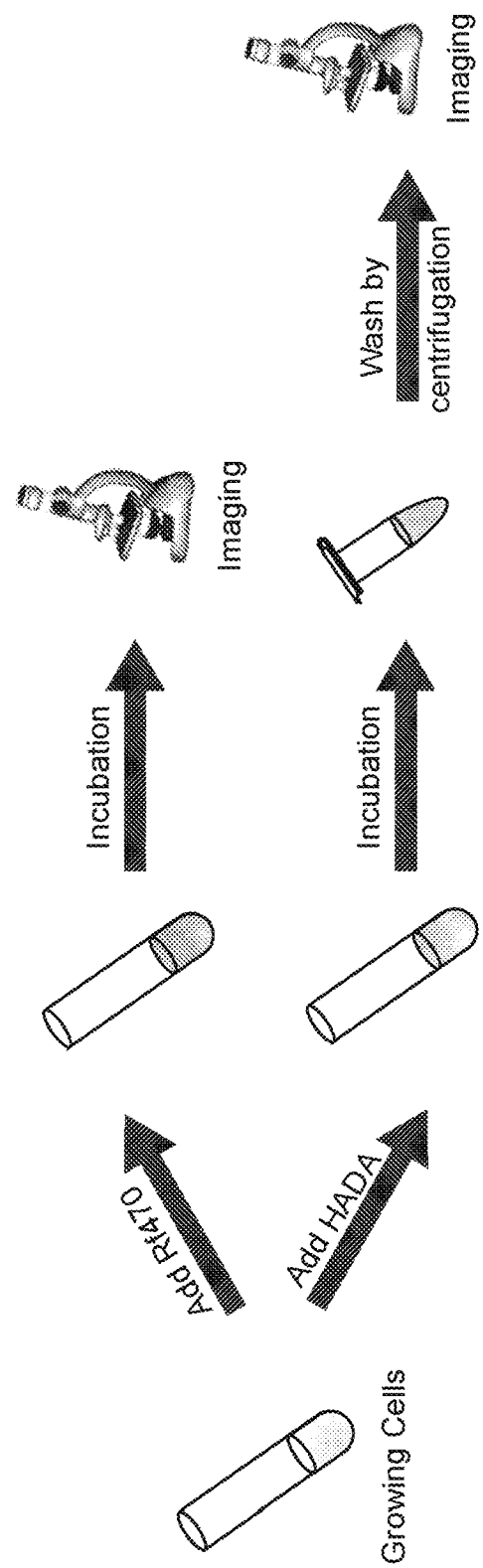
FIG. 3A depicts an exemplary FMR-DAAs and FDAA labeling protocol for visualizing a comparison of end-point imaging in live cells labeled with FMR-DAAs (for example, Rf470) or FDAA (for example, HADA).

An exemplary FMR-DAA and FDAA labeling protocol for visualizing a comparison of end-point imaging in live cells labeled with FMR-DAAs is shown in FIG. 3A Exemplary labeling of bacterial PG with FMR-probe-D-Lys conjugates having the FMR probe moiety of formula (I), wherein $R^1$ consists of a —CN moiety is illustrated in FIG. 3 (E-H). Exemplary labeling of bacterial PG with FMR-probe-D-Lys conjugates having the FMR probe moiety of formula (I), wherein $R^1$ consists of a —$CO_2H$ moiety is illustrated in FIG. 4.

In another aspect, an FMR-probe having the structure of formula (II) is provided:

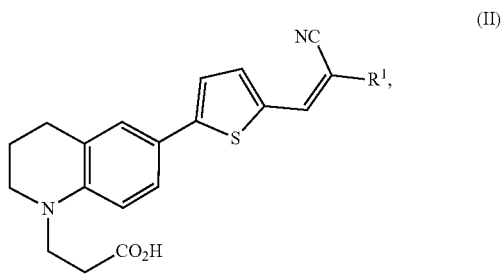

wherein $R^1$ is selected from —CN and —$CO_2H$.

Figure 5:
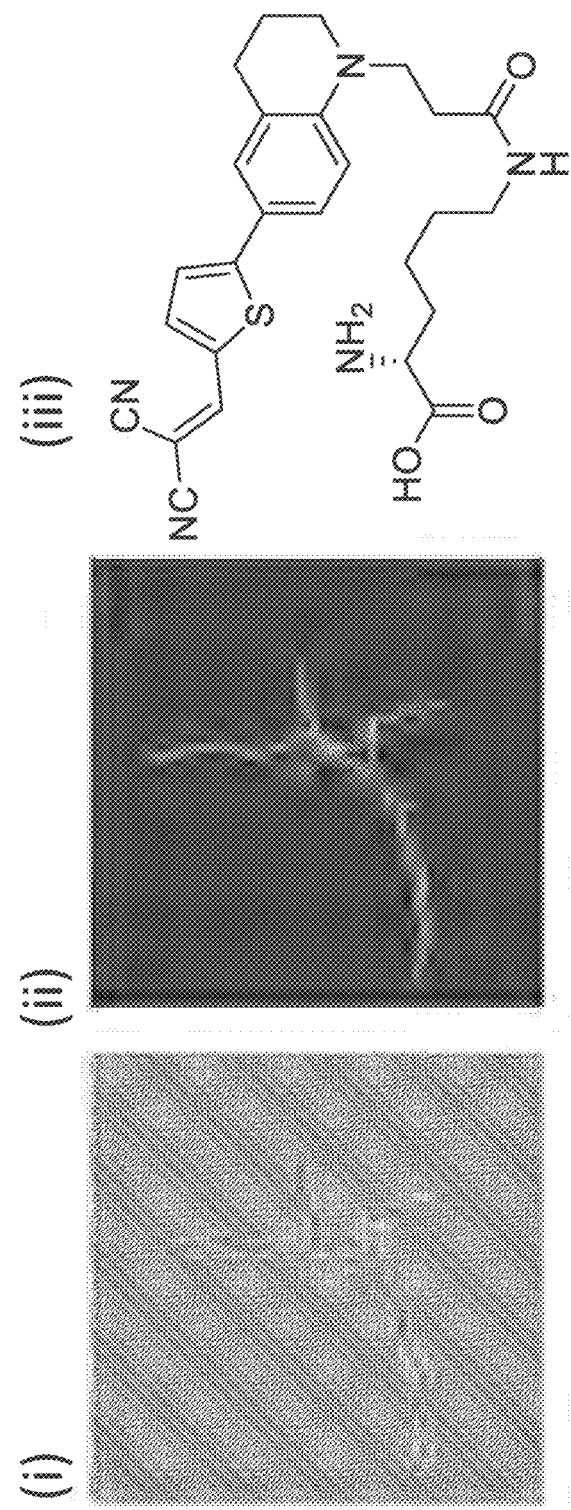
FIG. 5 depicts exemplary labeling (phase contrast in panel (i) and fluorescence contrast in panel (ii)) of *S. venezuelae*

The FMR-probes of formula (II) can be incorporated into D-amino acid backbones as described above. Exemplary labeling of bacterial PG with FMR-probe-D-Lys conjugates having the FMR probe moiety of formula (I), wherein $R^1$ consists of a —CN moiety is illustrated in FIG. 5. Exemplary labeling of bacterial PG with FMR-probe-D-Lys conjugates having the FMR probe moiety of formula (II), wherein $R^1$ consists of a —$CO_2H$ moiety is illustrated in FIG. 6.

Thiazole orange has long been known to have a high affinity for intercalation between DNA base pairs. Such probes can be modified with highly polar functional groups and substitutions to form non-planar conformations, which have been successful in preventing intercalation in DNA. A variety of other FMR architectures are also available in the art that can be used for this purpose (see, for example, the FMR architectures described in Uzhinov, B. M., V. L. Ivanov, and M. Y. Melnikov, "Molecular rotors as luminescence sensors of local viscosity and viscous flow in solutions and organized systems." Russ. Chem. Rev. 2011. 80:1179-1190 (2011)).

Fluorescent Muramylpentapeptide Precursor Units (FMPUs)

Compositions of the invention also include fluorescent muramylpentapeptide precursor units (FMPUs) having an NAM moiety with a peptide chain of three to five amino acids in which one or more of the amino acids in the stem peptide are FMR-probes as described herein.

Fluorescent Peptidoglycan Units (FPGUs)

Compositions of the invention also include fluorescent peptidoglycan units (FPGUs). The FPGUs have a FMPU as described herein linked to a NAG moiety.

In view of the foregoing, in one aspect of the invention, a modified amino acid comprising a D-amino acid covalently attached to a bioorthogonal tag is provided. In some respects, the bioorthogonal tag is selected from structures (I) and (II):

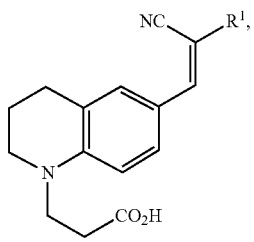

(I)

wherein $R^1$ is selected from —CN and —CO$_2$H; and

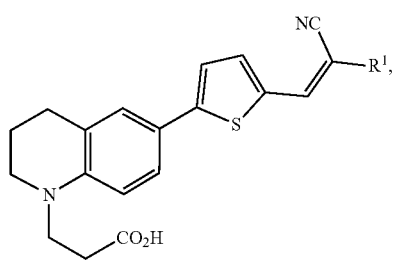

(II)

wherein $R^1$ is selected from —CN and —CO$_2$H.

Some preferred D-amino acids having molecular rotor compound designs for use in the present invention include the following:

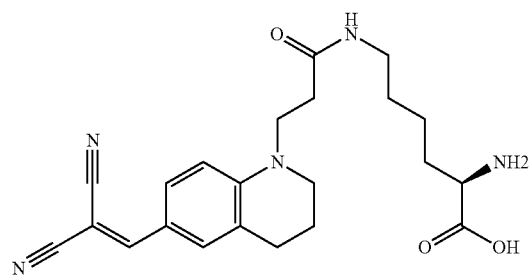 [SMILES: N#CC(C#N)=Cc1ccc2c(c1)CCCN2CCC(=O)NCCCC[C@@H](N)C(=O)O]

(N6-(3-(6-(2,2-dicyanovinyl)-3,4-dihydroquinolin-1(2H)-yl)propanoyl)-D-lysine (Rotor No. 1));

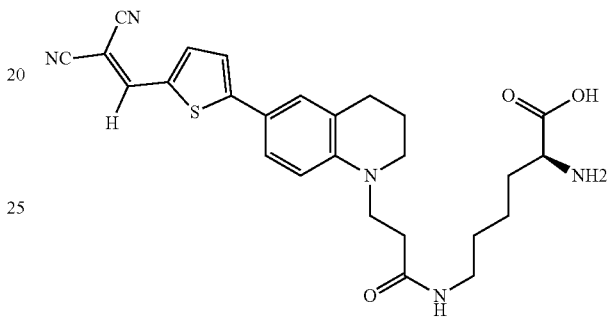

(N6-(3-(6-(5-(2,2-dicyanovinyl)thiophen-2-yl)-3,4-dihydroquinolin-1(2H)-yl)propanoyl)-D-lysine (Rotor No. 2));

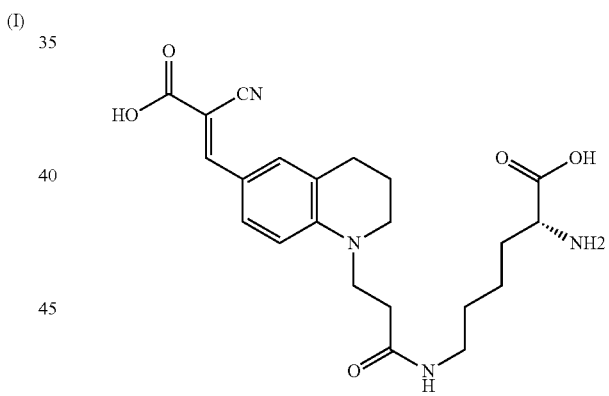

((E)-N6-(3-(6-(2-carboxy-2-cyanovinyl)-3,4-dihydroquinolin-1(2H)-yl)propanoyl)-D-lysine (Rotor No. 3); also known as Rf420);

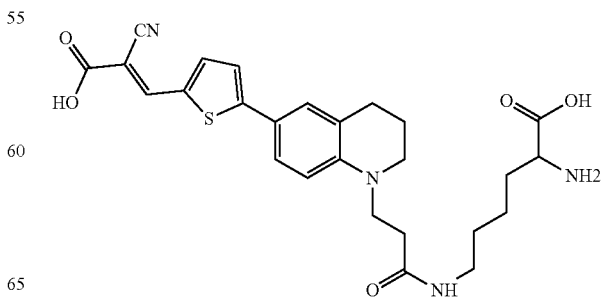

((E)-N6-(3-(6-(5-(2-carboxy-2-cyanovinyl)thiophen-2-yl)-3,4-dihydroquinolin-1(2H)-yl)propanoyl)-D-lysine (Rotor No. 4); also known as Rf470);

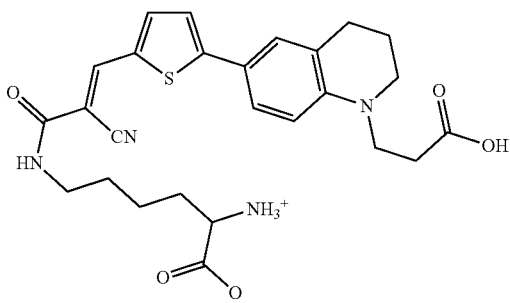

(E)-$N^6$-(3-(5-(1-(2-carboxyethyl)-1,2,3,4-tetrahydroquinolin-6-yl)thiophen-2-yl)-2-cyanoacryloyl)-L-lysine (Rf490), a structural isomer of Rf470, where D-lysine is coupled to the vinyl carboxylate group instead of the N-alkyl linker. A red-shift of 20 nm was found in the Max. $\lambda_{EX}$ compared to Rf470,

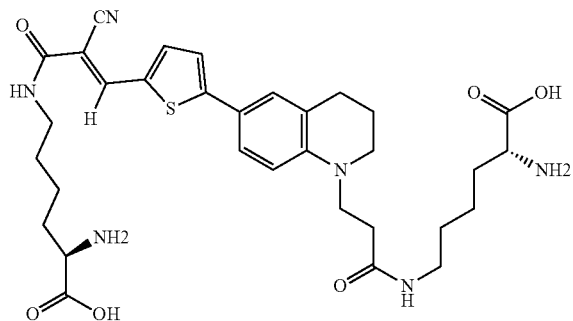 [SMILES: N#C/C(=C\c1ccc(-c2ccc3c(c2)CCCN3CCC(=O)NCCCC[C@@H](N)C(=O)O)s1)C(=O)NCCCC[C@@H](N)C(=O)O]

(6-(3-(6-(5-((E)-3-(((R)-5-amino-5-carboxypentyl)amino)-2-cyano-3-oxoprop-1-en-1-yl)thiophen-2-yl)-3,4-dihydroquinolin-1(2H)-yl)propanoyl)-D-lysine (Rotor No. 5), and

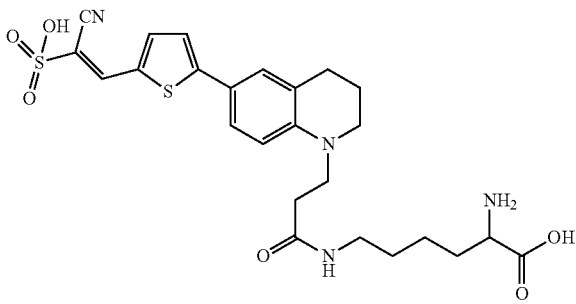 [SMILES: N#C/C(=C\c1ccc(-c2ccc3c(c2)CCCN3CCC(=O)NCCCCC(N)C(=O)O)s1)S(=O)(=O)O]

(E)-2-Cyano-2-sulfoethenyl]-2-thienyl}-1,2,3,4-tetrahydroquinol-1-yl)propionylamino]-2-aminohexanoic acid (Rotor No. 6).

Figure 3B:
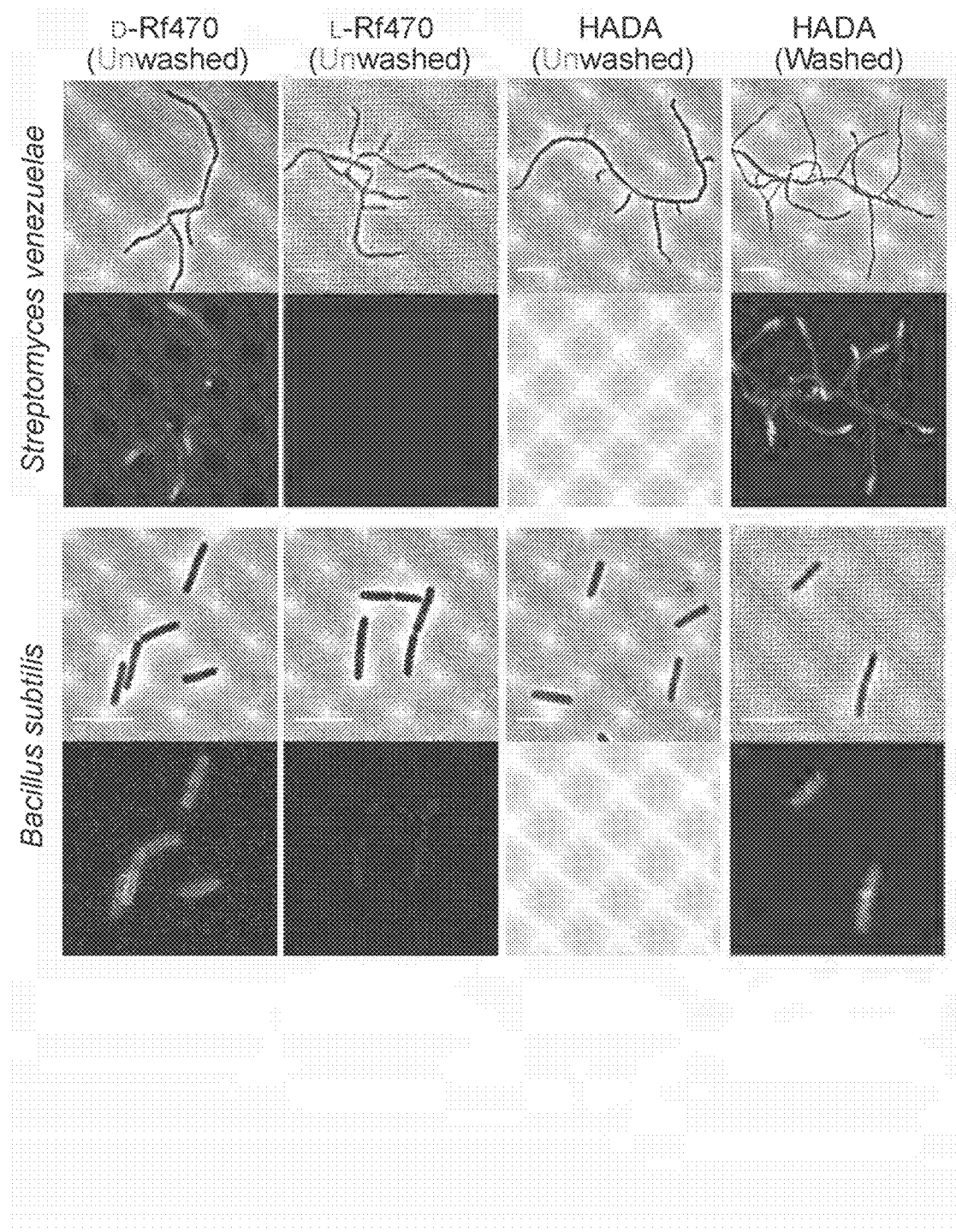
FIG. 3B depicts results of labeling *S. venezuelae* for 15 minutes (top eight image panels) (corresponding to ⅓ doubling time) and labeling in *B. subtilis* for 1 hour (bottom eight image panels) (corresponding to 3 doubling times) with D- and L-enantiomers of Rf470 (without washing prior to imaging) and with HADA (without or with washing prior to imaging). Identical labeling, imaging and processing conditions were used for the D- and L-enantiomer FMR-DAA (Rf470) labeling, as well as for unwashed and washed HADA labeling. Scale bar: 5 μm
Figure 4:
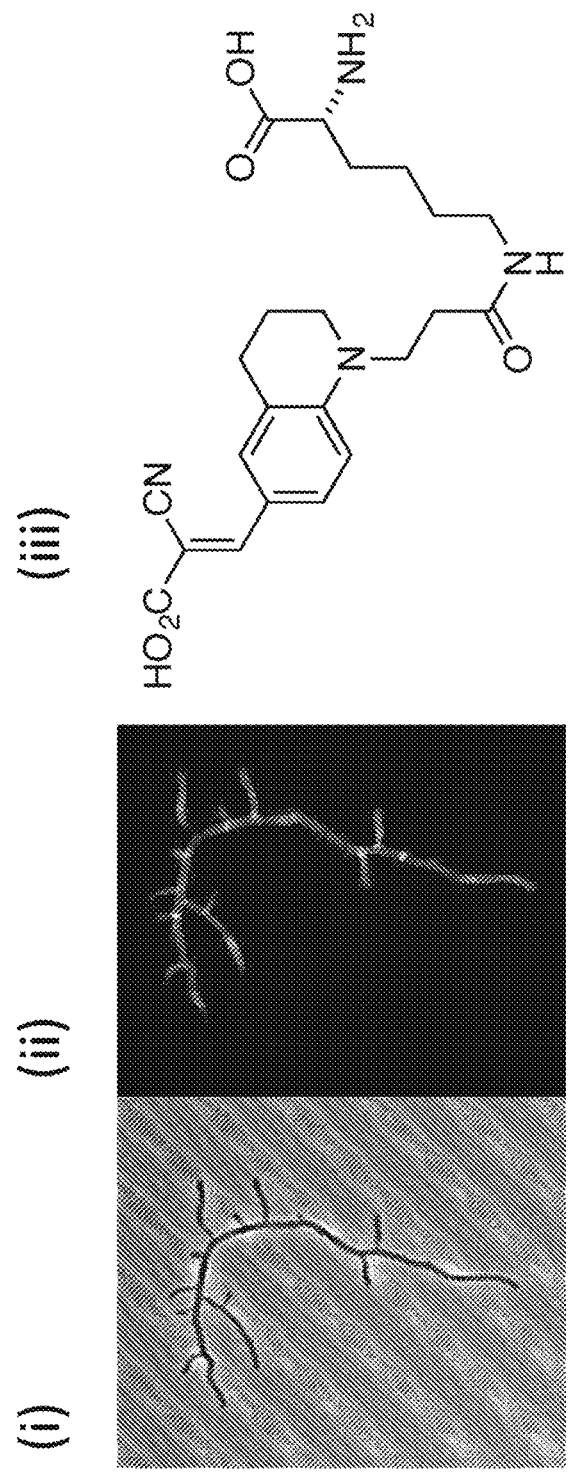
FIG. 4 depicts exemplary labeling (phase contrast in panel (i) and fluorescence contrast in panel (ii)) of *S. venezuelae* PG with FMR-probe-D-Lys conjugates having the FMR probe moiety of formula (I), wherein $R^1$ consists of a —CO$_2$H moiety (panel (iii))

An exemplary labeling of *S. venezuelae* and *B. subtilis* with Rf470 is illustrated in FIG. 3B.

Kits

Compositions of the invention also include kits having one or more FMR-probes or FMR-probe-D-Lys conjugates, FMPU and/or FPGU as described herein and optionally one or more labeled detecting agents for use in in situ labeling/probing of PG during biosynthesis, as well as for screening for bacterial cell wall-acting and/or cell wall-disrupting agents. The kits also can include additional reagents such as unlabeled D-amino acids (DAAs), labeled DDAs, unlabeled L-amino acids (LAAs) and/or labeled LAAs. The kits also can include positive and/or negative bacterial controls, where the controls are bacterial cells having unlabeled DAAs and LAAs or labeled DAAs and LAAs incorporated into PG in a cell wall. The kits may also include instructions for use, such as methods for incorporating the labeled regents and FMR-probes into cells.

As used herein, "kit" means any manufacture (e.g., a package or a container) having, for example, at least one FMR-probe, and a positive and/or negative control bacterium. The kit may be promoted, distributed, or sold as a unit for performing any of the methods described herein.

Though not necessarily required, kits preferably include instructions, procedures and/or directions that guide users or ones skilled in the art how to use the agents, reagents, and/or other components for their intended purpose. For example, kits can include a package insert describing procedures for carrying out any one of the methods described herein or analytical information for correlating the level of expression measured in live bacteria. Likewise, the package insert can include representative images of positive or negative samples with low or high levels of incorporation as compared to an appropriate control. The kits can be promoted, distributed or sold as units for performing the methods described herein.

The kits also can include a receptacle or other means for holding a sample to be evaluated for FMR-probe incorporation, and means for determining the presence and/or quantity of FMR-probe incorporation in live bacteria.

The kits also can include at least one buffer. Examples of buffers include, but are not limited to, cell isolation buffers, fixation buffers, lysis buffers, permeabilization buffers, sonication buffers, separation buffers, stabilization buffers and wash buffers. Though not limited, buffers include strong acids in combination with weak bases, strong bases in combination with weak acids, a combination of weak acids and bases, or even a small or low concentration (e.g., within the range from about 0.1 mM to about 10 mM) of an acid or base, in the absence of a conventional conjugate base or acid, respectively; typically, however another component of the mixture may provide such conjugate acid or base function. Examples of acids and bases, both in terms of ionization/dissociation strength (i.e., strong or weak) and type (i.e., inorganic or organic), are well known in the art.

Any or all of the kit components can be provided within containers that protect them from the external environment, such as in sealed containers.

Methods

Figure 1:
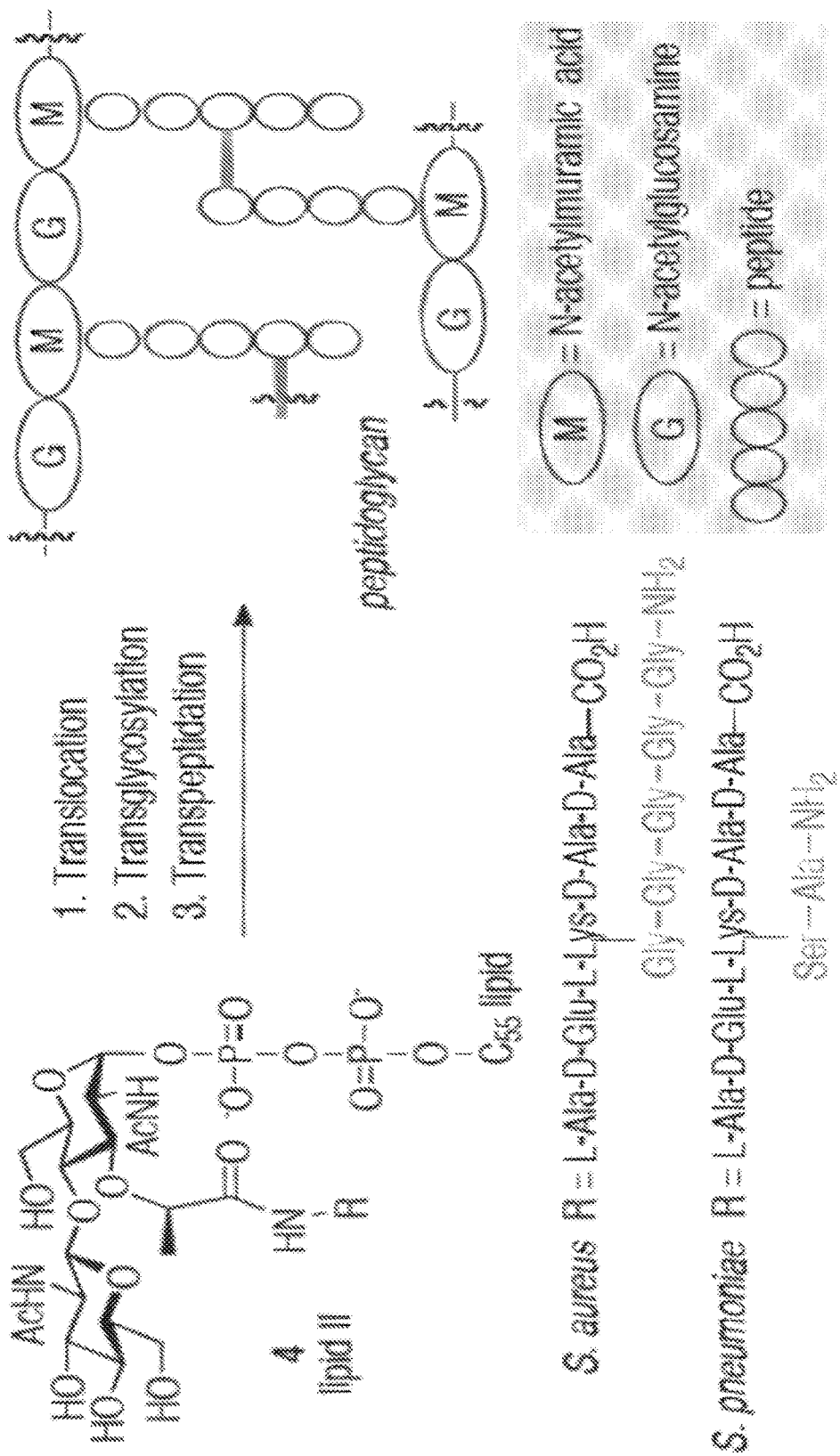
FIG. 1 shows the three general stages of PG biosynthesis and general structures of the NAM and NAG units of PG.

Methods include assessing bacterial cell wall biosynthesis (and PG recycling) in real time. As shown in FIG. 1, bacterial cell wall biosynthesis typically involves three steps: translocation, transglycosylation and transpeptidation. In the translocation and transglycosylation steps, carbohydrate backbone is formed by polymerization via glycosidic bond formation between the C(4)-hydroxyl of a membrane-bound lipid II intermediate and the anomeric center of a membrane-bound glycan strand. Bacterial transpeptidases mediate crosslinking of the resulting elongated glycan strand. The cross-link is installed via attack of an amino group, either from the Lys residue itself or from a short peptide chain appended to the Lys residue, onto the penultimate D-Ala residue of an adjacent pentapeptide strand and results in cleavage of the terminal D-Ala residue. This rigid macromolecular structure, essential to both Gram-negative and Gram-positive bacteria, enables bacterial cells to resist lysis and, subsequently, cell death resulting from high internal osmotic pressure.

These methods typically begin by providing live Gram-positive or Gram-negative bacteria with FMR-probe as described herein under conditions where the bacteria can covalently incorporate the FMR-probe into PG of a bacterial cell wall. The FMR-probe can be provided to organisms preferably within a given range of concentrations, for example, from about 0.1 µM to about 1 mM, as well as in any whole integer or fractional integer concentration thereof within this preferred range. The FMR-probe can also be provided to organisms at preferred concentrations, for example, at about 0.1 µM and about 1 mM. Other ranges are also possible besides this preferred range and fall within the scope of this disclosure, the specific identification of which depends upon the particular biological organism or system under study, as well as upon the nature of the FMR-probe(s) used, their physiochemical properties and uptake by the particular biological organism or system under study, as well as the experimental set-up and purpose of the study at hand, as one of skill in the art would understand.

Examples of suitable Gram-positive bacteria include, but are not limited to, *Actinomyces* spp., *Bacillus* spp., *Brachybacterium* spp., *Clostridium* spp., *Corynebacterium* spp., *Diplococcus* spp., *Enterococcus* spp., *Lactococcus* spp., *Listeria* spp., *Nocardia* spp., *Propionibacterium* spp., *Staphylococcus* spp., *Streptococcus* spp. *Streptomyces* spp. In the examples below, live *B. subtilis, B. conglomeratum, L. lactis, S. aureus, S. pneumoniae,* and *S. venezuelae.*

Examples of suitable Gram-negative bacteria include, but are not limited to, *Acinetobacter* spp., *Agrobacterium* spp., *Bordetella* spp., *Borrelia* spp., *Brucella* spp., *Burkholderia* spp., *Campylobacter* spp., *Caulobacter* spp., *Chlamydia* spp., *Enterobacter* spp., *Escherichia* spp., *Helicobacter* spp., *Hemophilus* spp., *Klebsiella* spp., *Legionella* spp., *Neisseria* spp., *Proteus* spp., *Pseudomonas* spp, *Salmonella* spp., *Shigella* spp., *Synechocystis* spp., *Verrucomicrobia* spp., *Vibrio* spp. and *Yersina* spp. In the examples below, live *A. tumefaciens, B. phytofirmans, C. crescentus, E. coli, Synechocystis* sp. PCC 6803 and *V. spinosum.*

Determination of the optimal concentration (or amount) of FMR-probe and the preferred ranges thereof for a particular organism is the subject of routine experimentation well within the purview of those skilled in the art. A typical route to ascertaining the optimal concentrations and preferred ranges of the FMR-probe described herein is to perform a dose response experiment, wherein the parallel populations of a given organism are contacted with different concentrations (or amounts) of a given FMR-probe, and the extent of incorporation of the compound(s) is assessed by biochemical assay (e.g., extent of compound labeling in PG fractions) and/or by visualization/detection methods (e.g., a plate reader, fluorescence microscopy, flow cytometry, mass spectrometry and the like). Other approaches to selecting the optimal concentration (of amount) of FMR-probe and the preferred ranges thereof for a particular organism are viable as well, as one skilled in the art would readily appreciate based upon this disclosure.

The methods also can include detecting the FMR-probe in the bacterial cell wall to verify that they have been incorporated. The FMR-probe can be detected via fluorescence (e.g., microscopy or a plate reader), flow cytometry and other methods, including but not limited to mass spectrometry, HPLC and ELISA, depending upon the type of label or reporter used.

Figure 3C:
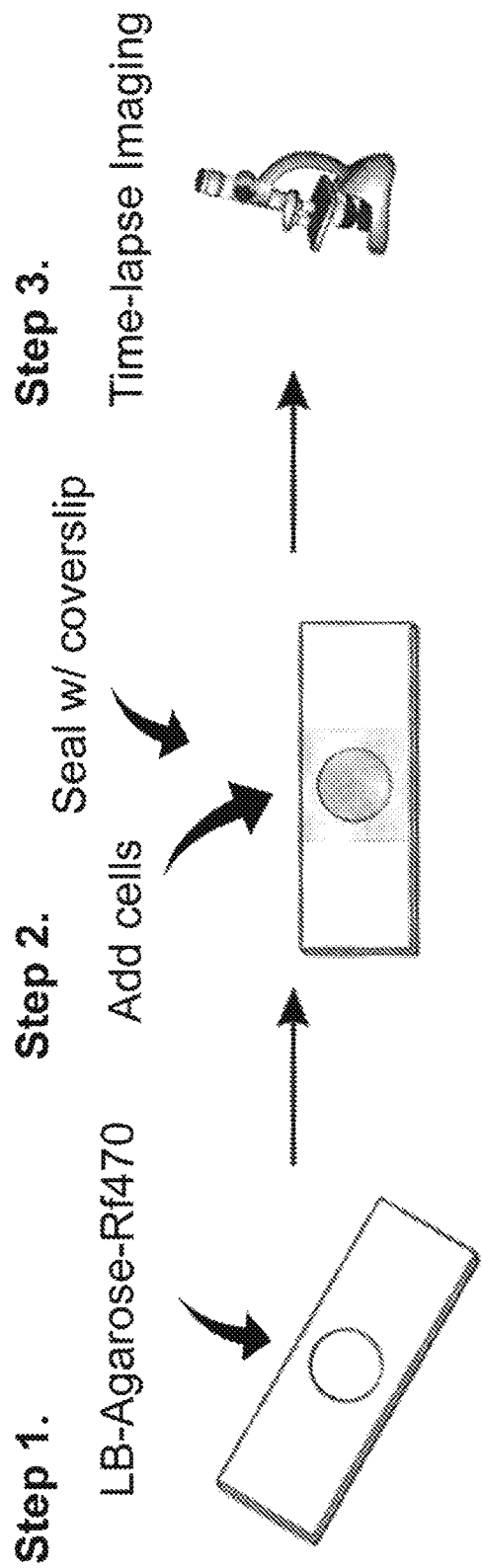
FIG. 3C depicts an exemplary scheme of sample preparation using cavity slides to visualize time-lapse microscopy of PG synthesis in *S. venezuelae*.
Figure 3D:
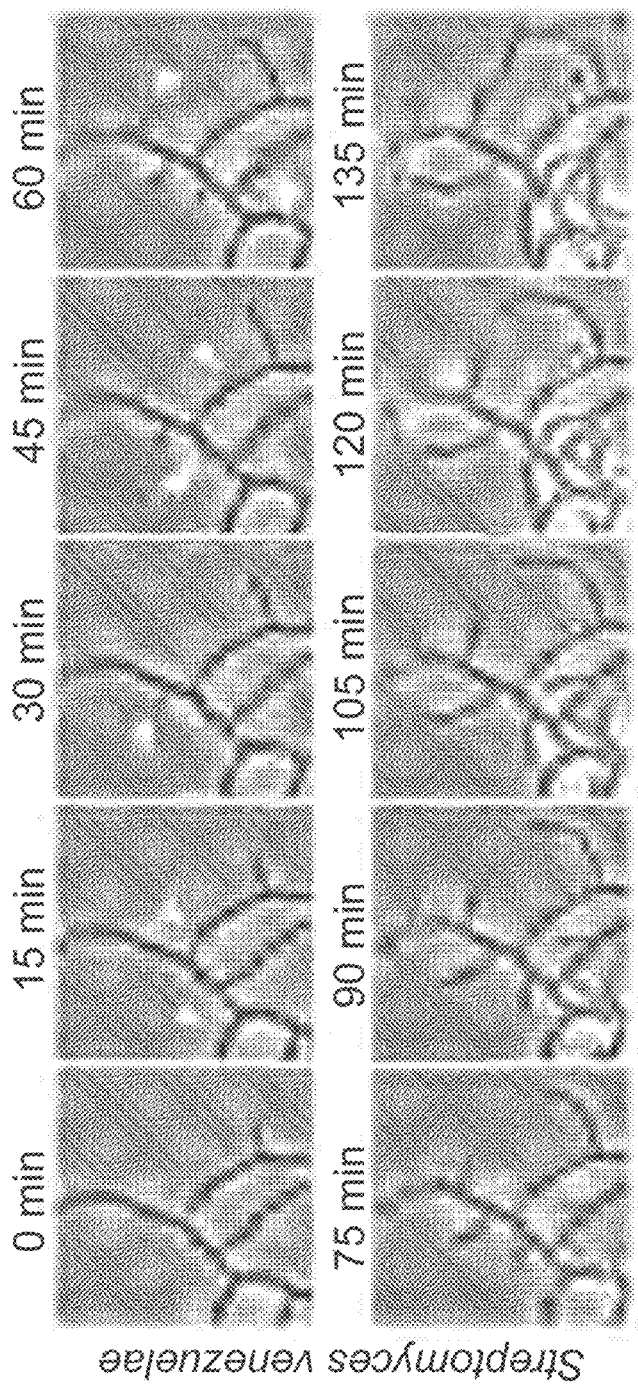
FIG. 3D depicts a montage of time-lapse Rf470 labeling in *S. venezuelae* (merged channel). Yellow arrowheads: newly formed septal PG; white arrowhead: newly formed branches. Scale bar: 5 μm
Figure 3E:
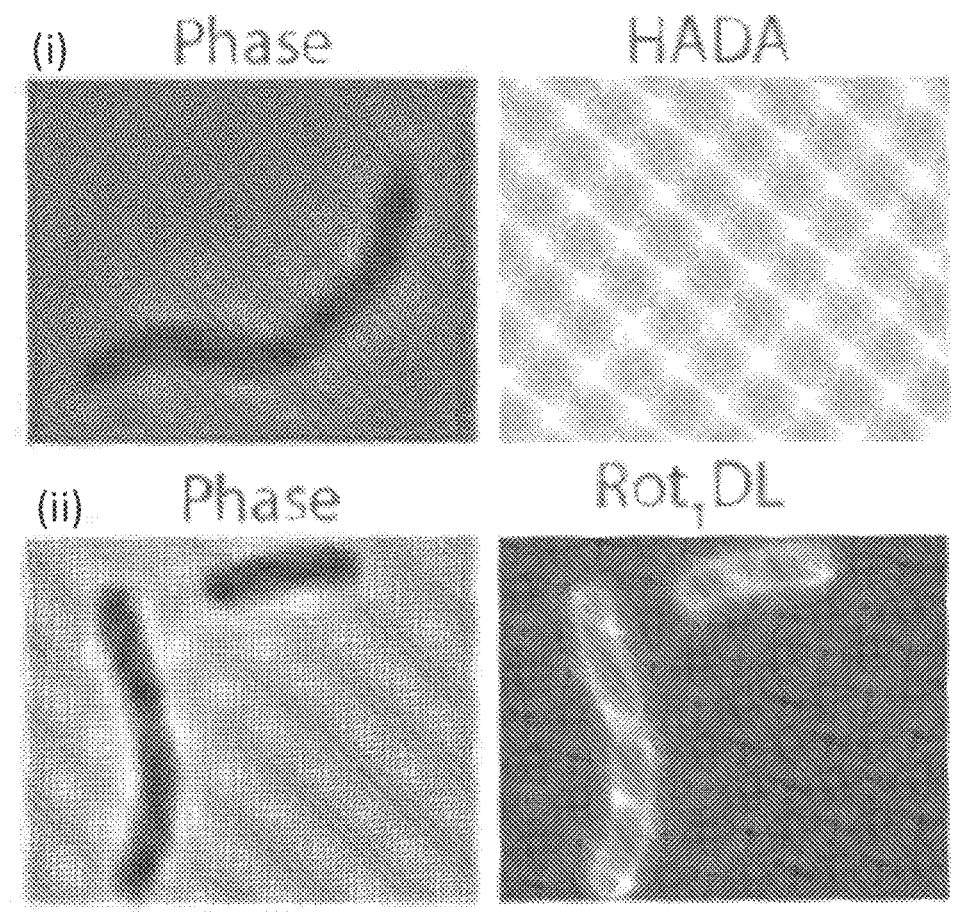
FIG. 3E depicts exemplary labeling of bacterial PG with HADA probe (panel (i)) and FMR-probe-D-Lys conjugates having the FMR probe moiety of formula (I), wherein $R^1$ consists of a —CN moiety (denoted as "Rot$_1$DL" (panel (ii))) without washing prior to fluorescence. Compared to conventional FDAAs (e.g., HADA), FMR-DAAs eliminate the need to wash excess probe.
Figure 3F:
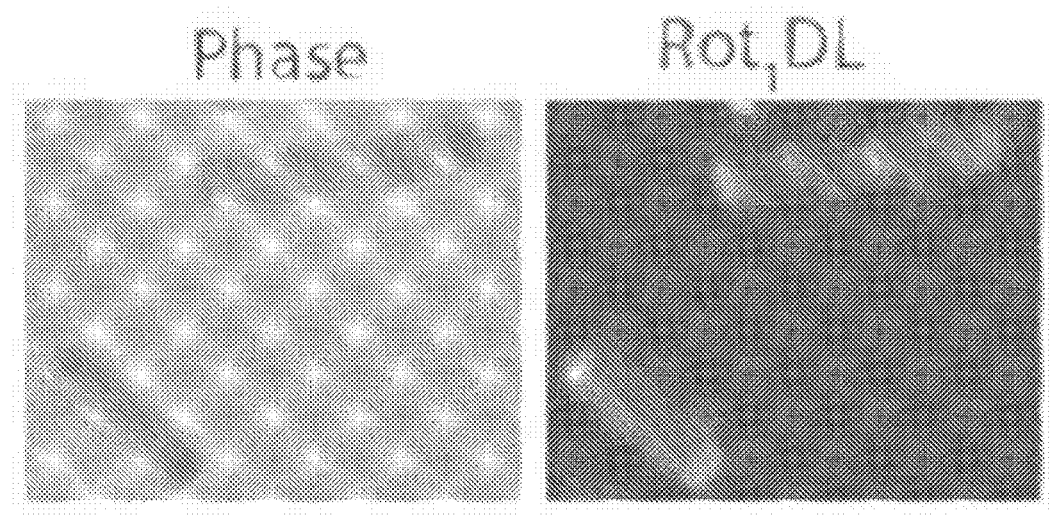
FIG. 3F shows that FMR-DAAs are covalently incorporated into PG sacculi for bacterial PG labeled with FMR-probe-D-Lys conjugates having the FMR probe moiety of formula (I), wherein $R^1$ consists of a —CN moiety (denoted as "Rot$_1$DL").
Figure 3G:
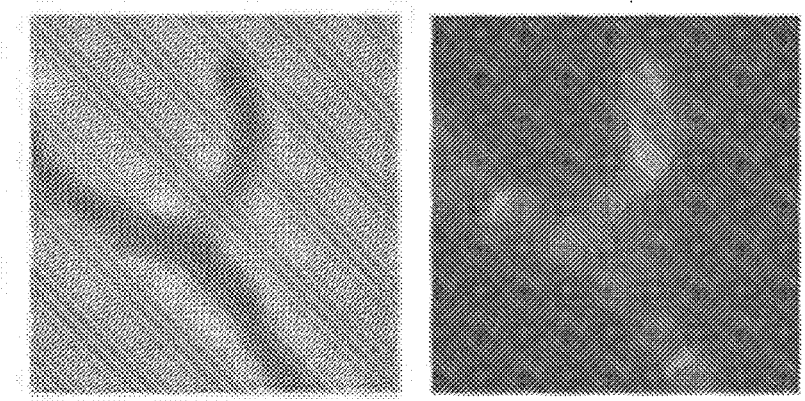
FIG. 3G shows that FMR-probe-D-Lys conjugates having the FMR probe moiety of formula (I), wherein $R^1$ consists of a —CN moiety (denoted as "Rot$_1$DL") has a low non-specific affinity to other cellular structures, and gives expected PG patterns only after a slight dilution by mounting on an agarose pad (panel (i)) as compared to the undiluted sample directly on coverslips (panel (ii)).
Figure 3G:
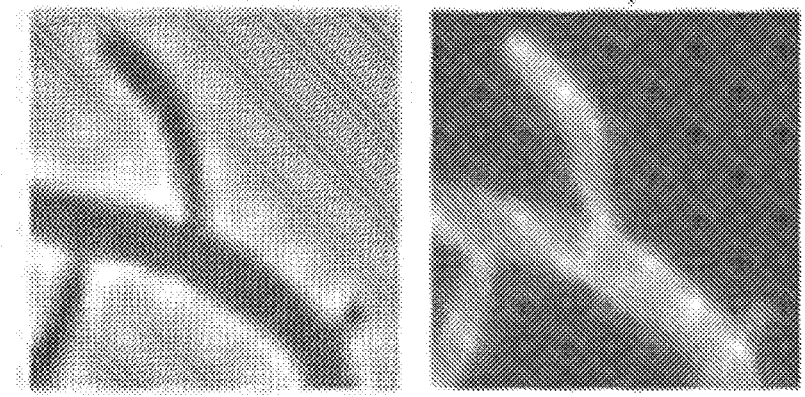
Figure 3H:
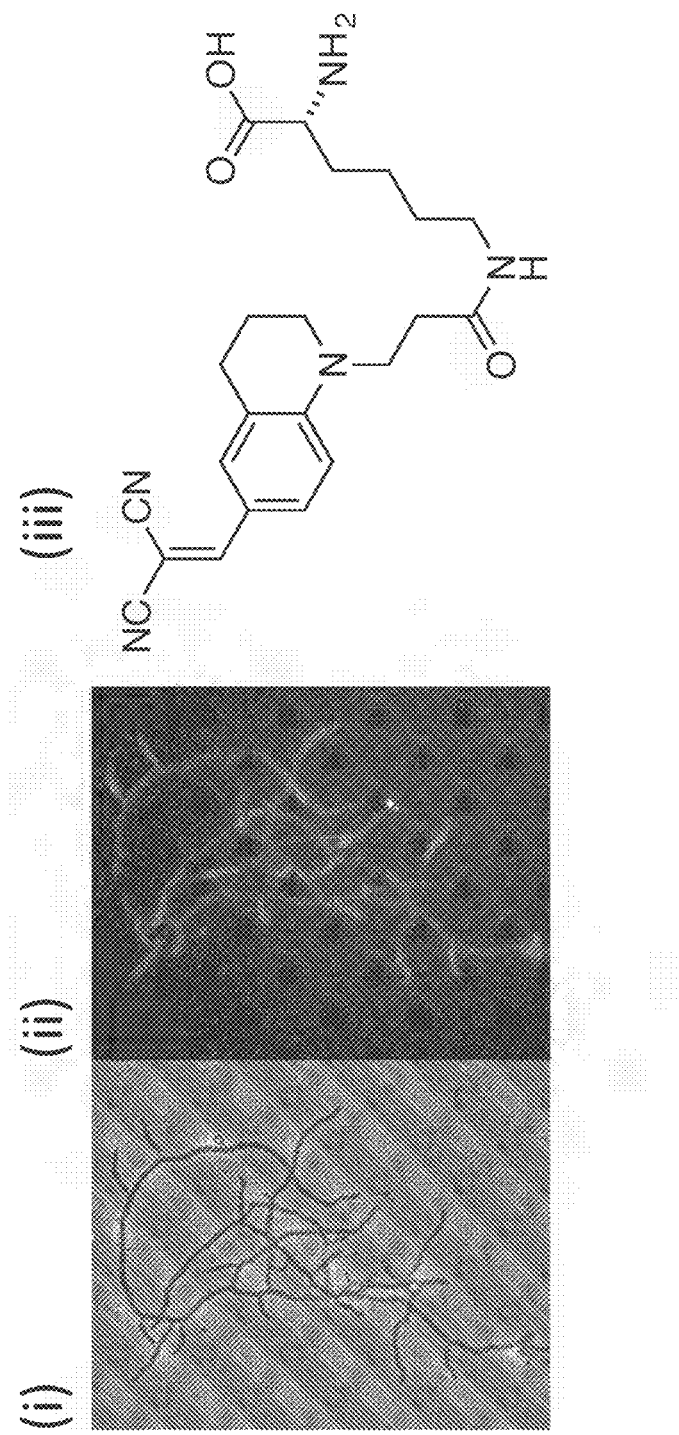
FIG. 3H depicts exemplary labeling (phase contrast in panel (i) and fluorescence contrast in panel (ii)) of *S. venezuelae* PG with FMR-probe-D-Lys conjugates having the FMR probe moiety of formula (I), wherein $R^1$ consists of a —CN moiety (panel (iii)).

The described FMR-probes and FMR-probe-D-Lys conjugates can be used to visualize PG synthesis in live bacterial cells. For example, FIG. 3C depicts an exemplary scheme of sample preparation using cavity slides to visualize time-lapse microscopy of PG synthesis in *S. venezuelae*. FIG. 3D depicts a montage of time-lapse Rf470 labeling in *S. venezuelae* PG.

In vitro real-time assays of transpeptidase enzyme activity using Rf470

We took advantage of the fact that FMR-DAAs are fluorogenic probes that fluoresce upon PG incorporation to develop a continuous, spectrophotometric assay to monitor the formation of transpeptidation product without the need of quenching and purification. The components of the assay included FMR-DAA probes as the fluorescence reporter, synthetic diacetyl-L-lysine-D-alanine-D-alanine as the substrate (acyl donor) and *Staphylococcus aureus* PBP4 enzyme. *S. aureus* PBP4 is known to have D,D-transpeptidation activity responsible for the highly cross-linked PG layer in staphylococci, as well as β-lactamase activity to degrade penicillin-like antibiotics. Knocking out PBP4 results in significantly decreased resistance to β-lactams in methicillin-resistant *S. aureus* (MRSA), suggesting that it is a valuable target for new antibiotic development.

Rf470, the synthetic substrate and *S. aureus* PBP4 were incubated in a 96-well plate and the emission fluorescence was measured overtime using a plate reader (5-minute interval, 1 hour in total, FIG. 12A). An increase in fluorescence intensity overtime was observed (FIG. 12B). The formation of cross-linked product was confirmed by reverse-phase HPLC and high-resolution mass spectrometry (FIG. 12C, D). Control experiments using the L-enantiomer of Rf470 showed no signal increase in this assay, which is consistent with the stereocenter selectivity of PBPs. To investigate the sensitivity of PBP4 toward antibiotics in this assay, a known effective inhibitor of *S. aureus* PBP4, cefoxitin, was added to the reaction, resulting in total inhibition of the D,D-transpeptidation activity. In contrast, when the reaction was treated with chloramphenicol, a ribosome peptidyl transferase inhibitor, the signal increase was comparable to the non-treated sample. These results indicate that signal increase in this assay results from the D,D-transpeptidase activity of *S. aureus*, and that FMR-DAAs could be employed for real-time monitoring of D,D-transpeptidase activity in vitro.

We further evaluated the utility of this assay for in vitro high-throughput screening for antibiotics. We tested various antibiotics (0.1 equiv. to the substrate) and measured the initial rate of fluorescence increase (FIG. 12E). As expected, antibiotics targeting the protein synthesis machinery showed no significant effect while β-lactam derivatives had an inhibitory activity: Cefoxitin and Carbenicillin inhibited the enzyme reaction almost completely; Penicillin G and Ampicillin showed partial inhibition; and Piperacillin, a selective inhibitor of *E. coli* PBP3, did not have a significant effect on *S. aureus* PBP4 activity. This result is consistent with published MIC values of these β-lactams against *S. aureus*. To further confirm the inhibitory effect of these β-lactams toward *S. aureus* PBP4, we performed a Nitrocefin assay, which tests PBP's β-lactamase activity, in the presence of the antibiotics. We found that, in the presence of Cefoxitin or Carbenicillin, Nitrocefin hydrolysis was strongly inhibited (>50%, FIG. 12F). However, Piperacillin and Ampicillin treatments did not inhibit PBP4s β-lactamase activity effectively, suggesting a low inhibitory effect toward PBP4. These results suggest that FMR-DAAs can be used to quantitatively measure the effect of β-lactams on the transpeptidation activity of PBP4 and potentially other PBPs. Because the assay bypasses the need for reaction quenching and product purification, the time required for data acquisition can be greatly reduced. We also note that this assay can be conducted in an end-point manner, providing an efficient way to test a large number of samples since only a single measurement is required per sample. End-point assays potentially enable high-throughput applications for drug screening and transpeptidation reaction studies.

In addition to PBPs, we tested the in vitro assay in other classes of transpeptidases: L,D-transpeptidase (Ldts) and Sortases. It is known that LdtA, encoded by *V. cholerae* vc1268, is responsible for 3'-3' cross-linkage formation. Incubation of LdtA with Rf470 and a synthetic tetrapeptide (diacyl-L-Ala-D-Glu-L-Lys-D-Ala) leads to a time-lapse increase of fluorescence signal, as seen in the PBP4 experiments. On the other hand, *S. aureus* Sortase A (SrtA) is responsible for anchoring surface proteins to PG through a sequence-specific transpeptidation reaction. It recognizes a conserved protein LPXTG motif, and cross-links it with PG pentaglycine in *S. aureus*. We incubated Sortase A with synthetic pentapeptide motif (LPETG) in the FMR-DAA assay, and observed an increase of Rf470 signal over time. Control experiments in the absence of the substrate led to no signal change. These results suggest that our in vitro FMR-DAA assay is highly applicable in transpeptidase activity measurement for studying PG-to-PG and PG-to-protein cross-linking reactions.

Screening Methodologies

The cell wall biosynthetic pathway is unique to bacterial cells; therefore, agents that inhibit steps within this pathway are anticipated to show selective toxicity toward bacterial cells. As such, methods of the invention also can include screening for putative cell wall-acting or cell wall-disrupting agents. As used herein, "cell wall-acting" means an ability of an agent to interfere with PG biosynthesis in a bacterial cell wall, especially at the transglycosylation step, as this step takes place on the outer leaflet of the cell membrane so cellular penetration is not a prerequisite for the agent to manifest its biological activity. As used herein, "cell wall-disrupting" means an ability of an agent to disrupt or weaken the integrity of PG in an existing bacterial cell wall.

The methods can begin by contacting bacteria with a putative cell wall-acting agent or putative cell wall-disrupting agent, where the agent is cell wall-acting if the agent interferes with ongoing peptidoglycan biosynthesis in a bacterial cell wall or is cell wall-disrupting if the agent weakens integrity of peptidoglycan in an existing bacterial cell wall. When screening for putative cell wall-acting agents, the bacteria can be co-contacted with FMR-probe as described herein simultaneously with the putative agent. When screening for putative cell wall-disrupting agents, the bacteria can have FMR-probe as described herein covalently incorporated into PG of the cell wall prior to being contacted with the putative agent.

The methods also can include detecting whether the FMR-probe have been incorporated in the bacterial cell wall or whether the FMR-probe remain in the bacterial cell wall. As noted above, the FMR-probe can be detected via fluorescence (e.g., via microscopy or a plate reader) and other methods, including but not limited to flow cytometry, mass spectrometry, HPLC and ELISA, depending upon the type of label or reporter used. The pattern and/or location of FMR-probe incorporation can be used to identify the bacteria (see, e.g., FIGS. 8 and 9).

The methods also can include comparing the results from the putative cell wall-acting agent or cell wall-disrupting agent with a known cell wall-acting agent or known cell wall-disrupting agent.

The compounds of the present disclosure have utility for identifying bacteria. As demonstrated in the Examples set forth herein, certain bacterial species display unique specificity for incorporating certain D-amino acids in PG and the bacteria cell wall. Thus, the use of the disclosed modified D-amino acids of the present disclosure enable identification of bacterial species by virtue of the pattern of labeling observed in the bacteria as a result of incorporation of the modified D-amino acids into PG of the bacterial cell wall.

In some respects, the D-amino acid of the modified amino is selected from the group consisting of 3-amino-D-Ala and D-Lys.

In another aspect of the invention, a muramylpentapeptide precursor unit comprising an N-acetyl muramic acid (NAM) moiety having a stem peptide of three to five amino acids is provided. One or more of the amino acids in the stem peptide comprises a modified amino acid as described above and optionally an additional modified amino acid, wherein the additional modified amino acid includes a clickable D-amino acid.

In another aspect of the invention, a peptidoglycan unit comprising the muramylpentapeptide precursor unit as described above covalently linked to an N-acetyl glucosamine (NAG) moiety is provided.

In another aspect of the invention, a live bacterial organism comprising a bacterium having a modified cell wall comprising modified peptidoglycan containing at least one modified amino acid as describe above, and optionally at least one additional modified amino acid, wherein the at least one additional amino acid includes a clickable D-amino acid.

In another aspect of the invention, a method of assessing bacterial cell wall synthesis in real time is provided. The method includes the step of providing live bacteria with a first amount of at least one modified amino acid as described above, and optionally a second amount of at least one additional modified amino acid that includes a clickable D-amino acid, under conditions sufficient for bacterial cell wall synthesis. The bacteria covalently incorporate the at least one modified amino acid and optionally the at least one additional amino acid into a stem peptide of peptidoglycan of the bacterial cell wall. In one respect, the first amount and second amount comprise a first concentration and a second concentration, respectively, wherein the first and second concentrations range from about and including 0.10 µM to about and including 1 mM. In further implementations of these methods, one can include the additional step of an additional step of detecting the at least one modified amino acid, and optionally the at least one additional modified amino acid incorporated into the stem peptide.

In the foregoing methods, the bacteria are Gram-positive bacteria or Gram-negative bacteria.

In another aspect of the invention, a method of screening for a putative cell wall-acting agent is provided. The method includes the step of co-contacting bacteria with an effective amount of an agent and an amount of at least one modified amino acid as described above, and optionally an amount at least one additional modified amino acid includes a clickable D-amino acid, under conditions sufficient to permit ongoing peptidoglycan biosynthesis in a bacterial cell wall. The agent comprises a cell wall-acting agent if the agent interferes with ongoing peptidoglycan biosynthesis in the bacterial cell wall. In some implementations of this method, one can include the additional step of detecting one or more modified amino acids incorporated in the bacterial cell wall. In some respects, the step of detecting one or more modified amino acid incorporated in the bacterial cell wall includes post-labeling the bioorthogonal tag with a label and visualizing or detecting the one or more labeled amino acids with microscopy, for example. As noted above, the FMR-probe can be detected via fluorescence (e.g., via microscopy or a plate reader) and other methods, including but not limited to flow cytometry, mass spectrometry, HPLC and ELISA, depending upon the type of label or reporter used. In some implementations of this method, one can include the additional step of comparing the amount and/or identity of incorporated modified amino acids in the bacterial cell wall resulting from contacting the bacteria with the agent with the corresponding amount and/or identity of incorporated modified amino acids in a bacterial cell wall resulting from contacting the bacteria with a known cell wall-acting agent.

In another aspect of the invention, a method of screening for a putative cell wall-disrupting agent is provided. The method includes the step of contacting modified bacteria with an amount of an agent. The agent includes a cell wall-disrupting agent if the agent weakens integrity of peptidoglycan in an existing bacterial cell wall. The modified bacteria have a modified cell wall containing modified peptidoglycan having at least one stem peptide containing at least one modified amino acid as described above, and optionally at least one additional modified amino acid that includes a clickable D-amino acid. In some implementations of this method, one can include the additional step of detecting one or more modified amino acids disrupted in the bacterial cell wall. In some respects, the step of detecting one or more modified amino acids disrupted in the bacterial cell wall includes post-labeling the bioorthogonal tag with a label and visualizing or detecting the one or more labeled amino acids with microscopy, for example. In some implementations of this method, one can include the additional step of comparing the amount and/or identity of disrupted D-amino acids in the bacterial cell wall resulting from contacting the bacteria with the agent with the corresponding amount and/or identity of disrupted D-amino acids in a bacterial cell wall resulting from contacting the bacteria with a known cell wall-disrupting agent.

In any of the foregoing methods employing the modified amino acids as described above, the bacteria can be Gram-positive bacteria or Gram-negative bacteria.

In another aspect of the invention, a method of identifying bacteria is provided. The method includes two steps. The first step includes contacting live bacteria with an amount of at least one modified amino acid as described above under conditions sufficient for ongoing bacterial cell wall synthesis. The bacteria covalently incorporate into peptidoglycan of a bacterial cell wall the at least one modified amino acid. The second step includes visualizing the label to determine an incorporation pattern of the at least one modified amino acid. The incorporation pattern identifies the bacteria.

In another aspect of the invention, a kit for incorporating modified amino acids into live bacteria is provided. The kit includes at least one modified amino acid as described above and a positive bacterial control and optionally a negative bacterial control. The positive bacterial control has at least one modified amino acid as described above incorporated into a stem peptide of peptidoglycan of the bacterial cell wall. The optional negative bacterial control, if included, does not have the modified amino acid as described above incorporated into a stem peptide of peptidoglycan of the bacterial cell wall. In some implementations of this kit, one can include at least one clickable D-amino acid and/or at least one reagent for post-labeling the bioorthogonal tag.

In another aspect, a method of wash-free labeling of bacterial cell wall peptides is provided. The method includes several steps. The first step includes contacting live bacteria with an amount of at least one modified amino acid of the first aspect under conditions sufficient for ongoing bacterial cell wall synthesis. The second step includes covalently incorporating into a peptide of a bacterial cell wall the at least one modified amino acid to form a covalent bond of the at least one modified amino acid with the peptide of the cell wall. The covalent modification of the peptide of the cell wall with the at least one modified amino acid results in producing a detectable label signal without requiring washing the bacterial cells following contacting the bacterial cells with the at least one modified amino acid.

In another aspect, methods for preparing the molecular rotor probes set forth herein, as well as methods for incorporating such molecular rotor probes into amino acids are provided herein. Such methods are described generally in the disclosure as well specifically by way of example in the EXAMPLES, as set forth below.

EXAMPLES

The invention will be more fully understood upon consideration of the following non-limiting examples, which are offered for purposes of illustration, not limitation.

Figure 2:
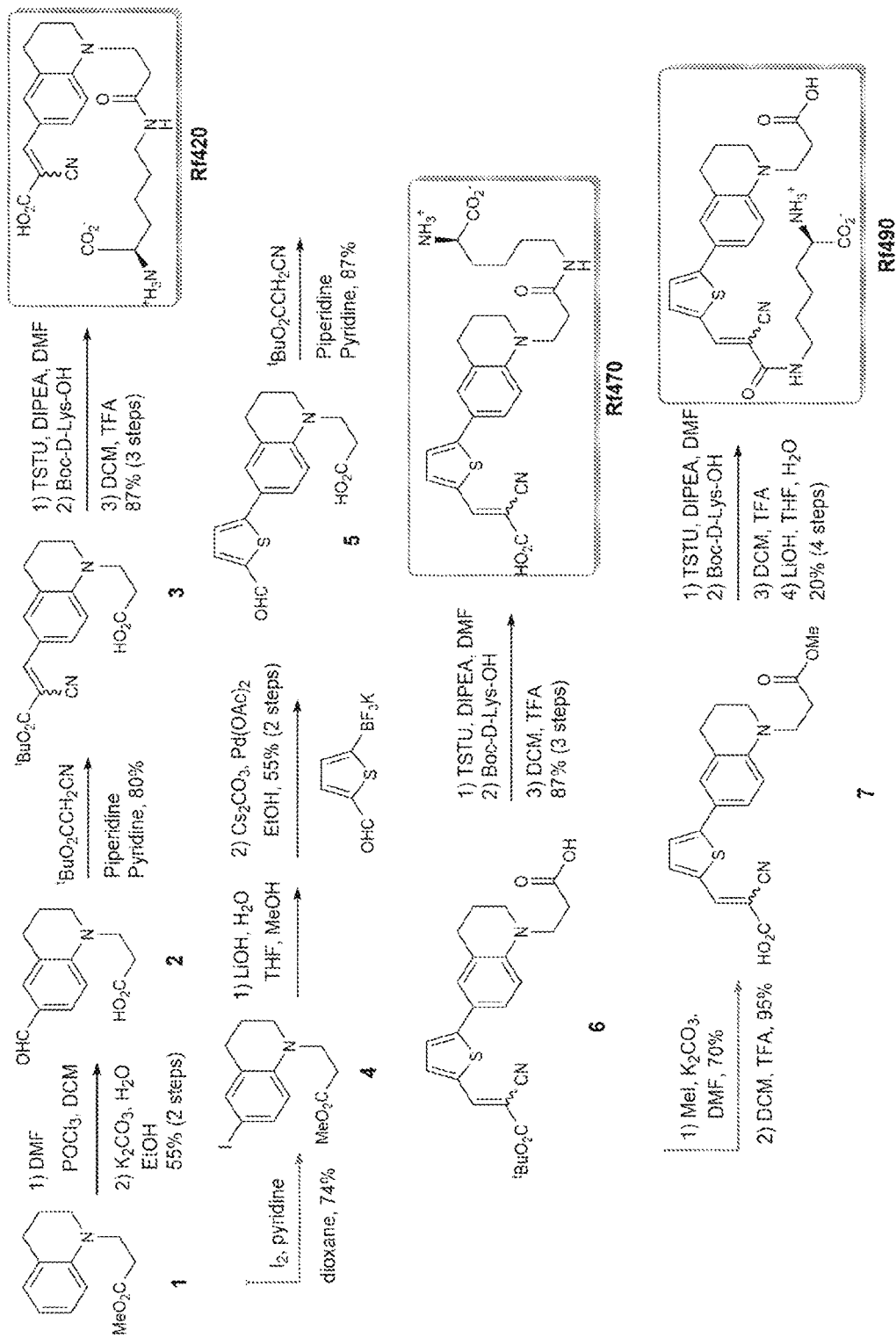
FIG. 2 depicts an exemplary scheme for the synthesis of FMR-probe-D-Lys conjugates, Rf420 (also known as Rotor No. 3), Rf470 (also known as Rotor No. 4) and Rf490.

Example 1. Fluorescent Molecular Rotor-Based D-Amino Acids: Synthesis and Biological Properties FIG. 2 depicts an exemplary scheme for the synthesis of FMR-probe-D-Lys conjugates, Rf420, Rf470 and Rf490. The synthesis of the intermediates and products are presented below.

Rotor No. 3 (Rf420) Designs

Intermediates were synthesized using a similar route and procedures from Sawada et al. (Sawada, S.; Iio, T.; Hayashi, Y.; Takahashi, S. *Anal Biochem* 1992, 204, 110), which is incorporated by reference in its entirety.

Methyl 3-(3,4-dihydroquinolin-1(2H)-yl)propanoate
(1)

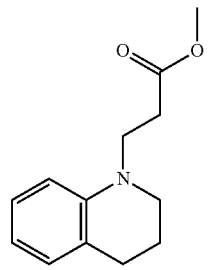

The following procedure was adapted from previously published literature. See Sawada, S., Iio, T., Hayashi, Y. & Takahashi, S. Fluorescent rotors and their applications to the study of G-F transformation of actin. *Anal. Biochem.* 204, 110-7 (1992) ("Sawada et al. (1992)"), which is incorporated by reference in its entirety. To a 250 mL round bottom flask containing trifluoroethanol (TFE, 38 mL, 1 M) were added 1,2,3,4-tetrahydroquinoline (4.71 mL, 37.54 mmol), methyl acrylate (10.2 mL, 112.62 mmol, 3 equiv.), and a stir bar. The reaction mixture was stirred at 100° C. for 16 h. The solvent and methyl acrylate leftover were removed by distillation at 130° C. The resulting crude product (7.8 g, 35.6 mmol, ~95% yield, light-yellow oil) was carried onto the next reaction without further purification. $^1$H NMR (400 MHz, Chloroform-d) δ 7.04 (t, J=7.8 Hz, 1H), 6.94 (d, J=7.4 Hz, 1H), 6.58 (d, J=7.6 Hz, 2H), 3.68 (d, J=1.4 Hz, 3H), 3.60 (t, J=7.3 Hz, 2H), 3.27 (t, J=5.6 Hz, 2H), 2.73 (t, J=6.5 Hz, 2H), 2.64-2.55 (m, 2H), 1.93 (p, J=6.1 Hz, 2H); ESI MS [M+H]248.1.

3-(6-formyl-3,4-dihydroquinolin-1(2H)-yl)propanoic acid (2)

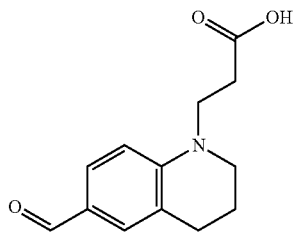

The following procedure was adapted from previously published literature (Sawada e al. (1992)). To a 250 mL round bottom flask was added 1 (8.23 g, 37.4 mmol), DMF (29 mL, 374 mmol, 10 equiv.), dichloromethane (74.8 mL, 0.5 M), and a stir bar. The reaction was cooled down to freezing point in an ice bath. Phosphoryl chloride (7 mL, 74.8 mmol, 2 equiv.) was then added to the reaction drop by drop with continuous stirring. The reaction was stirred on ice bath for 2 h. The resulting product was extracted with 100 mL dichloromethane and washed sequentially with 1M sodium hydroxide solution twice, 10% copper (II) sulfate solution (w/w) once, brine solution twice, and dried over magnesium sulfate. The crude product was purified using column chromatography (3:7 EtOAc/Hexane) to provide non-colored oil product (6.59 g, 26.7 mmol, 71% yield). The purified product (6.59 g, 26.7 mmol) was then added to a 100 mL round bottom flask, followed by addition of potassium carbonate (4.85 g, 29.4 mmol, 1.1 equiv.), ethanol/water mixture (9:1, 53.4 mL, 0.5 M), and a stir bar. The reaction was stirred at 95° C. for 16 h. The solvent was removed in vacuo. The reaction was neutralized with 1N HCl and then the product was extracted with 100 ml dichloromethane and washed sequentially with 1N HCl once, brine solution twice, and dried over magnesium sulfate. The solvent was removed in vacuo to provide the final product in green-yellow powder (4.86 g, 20.9 mmol, 78% yield). $^1$H NMR (500 MHz, DMSO-d$_6$) δ 9.58 (s, 1H), 7.50 (dd, J=8.6, 2.1 Hz, 1H), 7.37 (d, J=2.0 Hz, 1H), 6.69 (d, J=8.7 Hz, 1H), 3.61 (t, J=7.2 Hz, 2H), 3.37 (t, J=5.7 Hz, 2H), 2.69 (d, J=6.3 Hz, 2H), 2.52 (t, J=7.2 Hz, 2H), 1.87-1.78 (m, 21H); $^{13}$C NMR (126 MHz, DMSO-d$_6$) δ 189.94, 173.46, 150.04, 131.10, 130.39, 124.83, 122.18, 109.87, 49.41, 47.02, 31.41, 27.72, 21.42; TOF-HRMS (ES+) m/z (M+1) calculated for 234.1125, found: 234.1130.

(E)-3-(6-(3-(tert-butoxy)-2-cyano-3-oxoprop-1-en-1-yl)-3,4-dihydroquinolin-1(2H)-yl)propanoic acid (3)

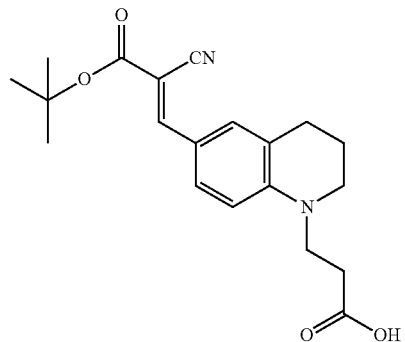 [SMILES: CC(C)(C)OC(=O)/C(C#N)=C/c1ccc2c(c1)CCCN2CCC(=O)O]

To a 250 mL round bottle flask was added 2 (3.47 g, 14.9 mmol), tert-butyl cyanoacetate (10.64 mL, 74.5 mmol, 5 equiv.), pyridine (30 mL, 0.5 M), pipyridine (1 mL), and a stir bar. The reaction was stirred at 90° C. for 16 h. The reaction was extracted with 100 mL ethyl acetate and washed sequentially with 1N HCl twice, brine solution twice and dried over magnesium sulfate. The solvent was removed in vacuo. The resulting product was purified using column chromatography (7:3 EtOAc/Hexane) to provide a yellow solid (4.2 g, 11.9 mmol, 80% yield). $^1$H NMR (500 MHz, Acetone-d$_6$) δ 7.93 (s, 1H), 7.82 (dd. J=8.9, 2.3 Hz, 1H), 7.66 (d, 1H), 6.79 (d, J=8.9 Hz, 1H), 3.75 (t, J=7.1 Hz, 2H), 3.52 (t, 2H), 2.75 (t, J=6.3 Hz, 2H), 2.68 (t, J=7.1 Hz, 2H), 1.94 (p, 2H), 1.54 (s, 9H); $^{13}$C NMR (126 MHz, Acetone) δ 173.15, 163.62, 154.01, 150.29, 133.46, 133.23, 123.35, 119.97, 118.17, 111.14, 95.54, 82.45, 50.39, 47.62, 31.62, 28.46, 28.22, 22.11; TOF-HRMS (ES+) m/z (M+1) calculated for 357.1809, found: 357.1812.

(E)-N6-(3-(6-(2-carboxy-2-cyanovinyl)-3,4-dihydroquinolin-1(2H)-yl)propanoyl)-D-lysine (Rotor No. 3) (Rf420)

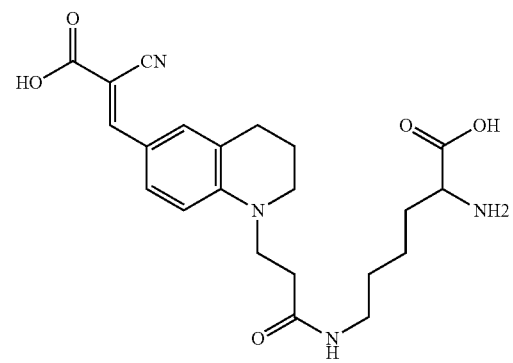 [SMILES: N#C/C(=C\c1ccc2c(c1)CCCN2CCC(=O)NCCCCC(N)C(=O)O)C(=O)O]

To a 25 mL round bottom flask was added 3 (143 mg, 0.4 mmol), TSTU (121 mg, 0.4 mmol, 1 equiv), anhydrous DMF (4 mL, 0.1 M), and diisopropylethylamine (0.2 mL, 1.2 mmol, 3 equiv) under argon. The reaction was stirred at room temperature for 2 h. Boc-D-Lys-OH (197 mg, 0.8 mmol, 2 equiv) was added in one portion and the reaction was allowed to continue stirring overnight. The reaction was diluted with 100 mL ethyl acetate and washed sequentially with 1 N HCl once, H₂O twice, and brine once. The organic layer was dried over anhydrous magnesium sulfate, filtered, and the solvent was removed in vacuo. The crude material was dissolved in TFA/DCM (1:1, 3 mL) and stirred at room temperature for 1 h. The solvent was removed in vacuo. The product was purified via reverse phase HPLC (10-90% MeCN/H₂O (v/v) over 10 min, 0.1% TFA (v/v), rt=7 min) to yield Rf420-TFA salt (150 mg, 0.35 mmol, 87% yield). ¹H NMR (500 MHz, Methanol-d₄) δ 7.96 (s, 1H), 7.74 (dd, J=8.9, 2.3 z, 1H), 7.60 (d, J=2.2 Hz, 1H), 6.75 (d, J=8.9 Hz, 1H), 3.90 (dd, J=6.8, 5.9 Hz, 1H), 3.72 (t, J=6.9 Hz, 2H), 3.45 (dd, J=6.6, 4.8 Hz, 2H), 3.17 (t, 2H), 2.74 (t, J=6.3 Hz, 2H), 2.50 (t, J=6.9 Hz, 2H), 1.98-1.80 (m, 4H), 1.56-1.37 (m, 4H); ¹³C NMR (126 MHz, CD₃OD) δ 173.80, 171.97, 167.22, 155.66, 151.04, 133.89, 133.83, 123.84, 120.42, 119.02, 111.53, 93.85, 53.94, 50.82, 40.00, 34.48, 31.18, 29.84, 28.85, 28.75, 23.35, 22.51; TOF-HRMS (ES+) m/z (M+1) calculated for 429.2132, found: 429.2138.

Rotor No. 4 (Rf470) Designs

Methyl 3-(6-iodo-3,4-dihydroquinolin-1(2H)-yl)propanoate (4)

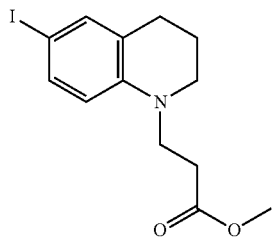 [SMILES: COC(=O)CCN1CCCc2cc(I)ccc21]

The following procedure was adapted from previously published literature. See Shao, J. et al. Thiophene-Inserted Aryl-Dicyanovinyl Compounds: The Second Generation of Fluorescent Molecular Rotors with Significantly Redshifted Emission and Large Stokes Shift. *European J. Org. Chem.* 2011, 6100-6109 (2011) ("Shao et al. (2011)"), which is incorporated by reference in its entirety. To a solution of 1 (16.5 g, 75 mmol) in [dioxane:pyridine (1:1)] (150 mL) at 0° C. was added molecular iodine (57.1 g, 225 mmol). After 30 minutes, the ice bath was removed and the mixture was allowed to reach room temperature after 1 hour. TLC and mass spec indicated reaction completion and so the reaction mixture was quenched by the addition of sat. Na₂S₂O₃ (200 mL) and then concentrated under reduced pressure. The aqueous remainder was then extracted with CH₂Cl₂ (2×200 mL). The combined organic layer was washed with water (100 mL) and brine (100 mL) then dried over MgSO₄ and concentrated in vacuo to provide a burgundy oil (19.2 g, 55.6 mmol, 74% yield) that was used directly in the next reaction. ¹H NMR (400 MHz, Chloroform-d) δ 7.28 (dd, J=8.7, 2.2 Hz, 1H), 7.21 (dt, J=2.1, 1.0 Hz, 1H), 6.35 (d, J=8.7 Hz, 1H), 3.68 (s, 3H), 3.58 (dd, J=8.0, 6.5 Hz, 2H), 3.27 (t, 2H), 2.69 (t, J=6.4 Hz, 2H), 2.57 (t, 2H), 1.90 (p, 2H); ESI MS m/z (M+H) found 346.0.

Potassium trifluoro(5-formylthiophen-2-yl)borate 5-formyl-2-thienylboronic acids (7.6 g, 49 mmol) was dispersed in [MeOH:H₂O (4:1)(250 mL)] then KHF₂ (11.5 g, 147 mmol) was added. The reaction mixture was stirred for 12 hours at room temperature then concentrated in vacuo to provide a grey solid that was carried on directly to the next reaction.

3-(6-(5-formylthiophen-2-yl)-3,4-dihydroquinolin-1(2H)-yl)propanoic acid (5)

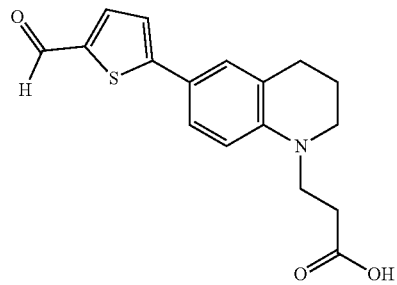 [SMILES: O=Cc1ccc(-c2ccc3c(c2)CCCN3CCC(=O)O)s1]

The following procedure was adapted from previously published literature (Shao et al. (2011)). To a solution of 4 (15.2 g, 44 mmol) in [THF:MeOH:H₂O (2:2:1×375 mL)] at 0° C. was added LiOH·H₂O (2 g, 48 mmol). The reaction mixture was closely monitored by TLC, and upon consumption of starting material was immediately quenched by the addition of 0.5 M HCl (100 mL) and the reaction solvents were removed in vacuo. The residue was re-constituted with EtOAc (200 mL) and the organic extract was washed with water (100 mL) and brine (100 mL) then dried over MgSO₄. The organic solution was concentrated in vacuo to a beige solid (13.5 g, 40 mmol, 92% yield) which was submitted directly to the next reaction. ESI MS m/z (M+H) found 332.0. To the potassium organotrifluoroborate salt was added the beige solid intermediate (13.5 g, 40 mmol) and EtOH (200 mL), followed by Cs₂CO₃ (31.8 mL, 98 mmol) and Pd(OAc)₂ (90 mg, 0.4 mmol). The reaction mixture was heated to reflux (120° C.) until the starting material was consumed, as indicated by TLC. The reaction mixture was concentrated in vacuo, diluted with CH₂Cl₂ (300 mL), and then slowly quenched by the addition of 8 M HCl (150 mL). The organic layer was washed with water (200 mL), brine (200 mL), then dried over MgSO₄ and concentrated under reduced pressure. The residue was purified by flash column chromatography to provide an orange solid (7.58 g, 24 mmol, 60% yield). H NMR (400 MHz, Chloroform-d) 9.81 (s, 1H), 7.66 (d, J=4.0 Hz, 1H), 7.39 (d, J=8.9 Hz, 1H), 7.28 (s, 1H), 7.21 (d, J=4.0 Hz, 1H), 6.61 (d, J=8.6 Hz, 1H), 4.15 (q, J=7.1 Hz, 2H), 3.66 (t, J=7.2 Hz, 2H), 3.36 (t, J=5.6 Hz, 2H), 2.78 (t, J=6.4 Hz, 2H), 2.61 (t, J=7.1 Hz, 2H), 1.96 (p, J=6.0 Hz, 2H), 1.27 (t, 3H); ¹³C NMR (126 MHz, DMSO) δ 183.03, 173.18, 154.91, 145.82, 139.69, 139.04, 126.80, 125.52, 122.49, 121.80, 119.40, 110.43, 48.71, 46.47, 30.92, 27.35, 21.31. ESI MS [M+H]316.1. R_f=0.4 [Hexane:{EtOAc:EtOH(3:1) 2% AcOH}(2:1)]; TOF-HRMS (ES+) m/z (M+1) calculated for 316.0963, found: 316.1005.

(E)-3-(6-(5-(3-(tert-butoxy)-2-cyano-3-oxoprop-1-en-1-yl)thiophen-2-yl)-3,4-dihydroquinolin-1(2H)-yl)propanoic acid (6)

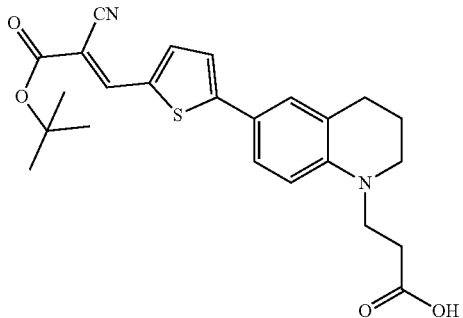 [SMILES: CC(C)(C)OC(=O)/C(C#N)=C/c1ccc(-c2ccc3c(c2)CCCN3CCC(=O)O)s1]

The thiophene aldehyde derivative (3.5 g, 11.1 mmol, 5) was dissolved in pyridine (55 mL). To this dark solution was added tert-butyl 2-cyanoacetate (8 mL, 55.5 mmol) and piperidine (5 mL). Upon addition of the piperidine, the solution turned dark, cherry red. The mixture was then heated to 90° C. for 18 hours. HPLC and TLC indicated full consumption of starting material and so the solution was concentrated under reduced pressure and solvents were removed azeotropically with toluene. The residue was dissolved in EtOAc (200 mL), then washed with 1 M HCl (100 mL), water (100 mL), brine (100 mL), then dried over $Na_2SO_4$ then concentrated in vacuo to provide dark red/black highly viscous oil which solidified to a glass upon standing. The material was sufficiently pure to be carried on to the next reaction (4.2 g, 9.66 mmol, 87% yield). An analytical sample was prepared by preparative HPLC. $^1H$ NMR (400 MHz, Chloroform-d) δ 8.16 (s, 1H), 7.63 (d, J=4.1 Hz, 1H), 7.43 (dd, J=8.6, 2.3 Hz, 1H), 7.31 (d, J=2.3 Hz, 1H), 7.21 (d, J=4.1 Hz, 1H), 6.61 (d, J=8.7 Hz, 1H), 3.69 (t, J=7.1 Hz, 2H), 3.38 (t, J=5.7 Hz, 2H), 2.80 (t, J=6.3 Hz, 2H), 2.69 (t, J=7.1 Hz, 2H), 1.99 (p, J=11.9, 6.1 Hz, 2H), 1.57 (s, H); $^{13}C$ NMR (126 MHz, $CDCl_3$) δ 177.05, 162.59, 156.18, 146.06, 145.73, 139.71, 132.91, 127.69, 125.93, 123.49, 121.82, 121.18, 116.89, 110.96, 97.36, 83.23, 49.70, 47.13, 31.25, 28.17, 27.96, 21.82; TOF-HRMS (ES+) m/z (M+1) calculated for 439.1692, found: 439.1709.

(E)-$N^6$-(3-(6-(5-(2-carboxy-2-cyanovinyl)thiophen-2-yl)-3,4-dihydroquinolin-1(2H)-yl)propanoyl)-D-lysine (Rotor No. 4) (Rf470)

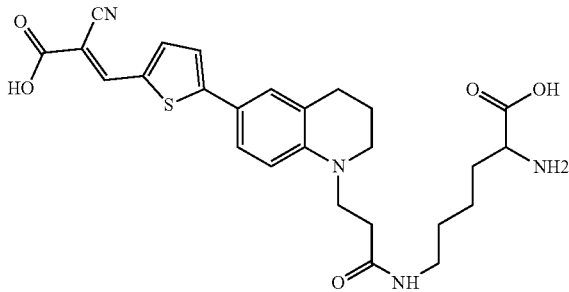 [SMILES: N#C/C(=C\c1ccc(-c2ccc3c(c2)CCCN3CCC(=O)NCCCCC(N)C(=O)O)s1)C(=O)O]

A solution of 6 (220 mg, 0.5 mmol) in DMF (5 mL) was purged with Argon gas. After 15 minutes, TSTU (151 mg, 0.5 mmol) and DIEA (0.25 ml, 1.5 mmol) were added, and the mixture was stirred for 2 hours at room temperature. Progress of the TSTU activation was monitored by HPLC and mass spectrometry. Once starting material was fully consumed, Boc-D-lysine (123 mg, 0.5 mmol) was added at once, and the mixture was stirred at room temperature for 20 hours. The reaction mixture was diluted with EtOAc (50 mL) and 1 M HCl (50 mL), followed by extraction with EtOAc (2×50 mL), wash with brine (50 mL), dried over $MgSO_4$ and then concentrated in vacuo. The crude residue was diluted with $CH_2Cl_2$ (3 mL) and TFA (3 mL). The solution was stirred at room temperature for 2 hours and then concentrated to a red residue that was purified by preparative HPLC (10-90% MeCN/$H_2O$ over 10 min, rt=8 min). The fractions containing the product were lyophilized to provide Rf470·TFA salt (272 mg, 43.5 mmol, 87% yield). $^1H$ NMR (500 MHz, DMSO-$d_6$) δ 8.35 (d, J=1.9 Hz, 1H), 7.89 (dd, J=4.2, 2.0 Hz, 1H), 7.82 (t, J=5.6 Hz, 1H), 7.46-7.44 (m, 1H), 7.42 (d, 1H), 7.31 (d, J=2.6 Hz, 1H), 6.69 (d, J=8.7 Hz, 1H), 3.83 (t, J=6.4 Hz, 1H), 3.57 (t, J=7.1 Hz, 2H), 3.32 (t, J=5.6 Hz, 2H), 3.06 (q, J=6.4 Hz, 2H), 2.73 (t, J=6.4 Hz, 2H), 2.37 (t, J=7.0 Hz, 2H), 1.91-1.71 (m, 4H), 1.39 (ddd, J=35.7, 10.4, 6.3 Hz, 4H), $^{13}C$ NMR (126 MHz, DMSO) δ 171.06, 170.41, 164.13, 155.71, 146.53, 146.23, 142.33, 131.61, 126.82, 125.71, 122.53, 121.88, 119.11, 117.01, 110.60, 95.21, 51.93, 48.80, 47.27, 38.19, 32.58, 29.70, 28.57, 27.37, 21.79, 21.29; TOF-HRMS (ES+) m/z (M+1) calculated for 511.2015, found: 511.1991.

Rf490 Designs (E)-2-cyano-3-(5-(1-(3-methoxy-3-oxopropyl)-1,2,3,4-tetrahydroquinolin-6-yl)thiophen-2-yl)acrylic acid (7)

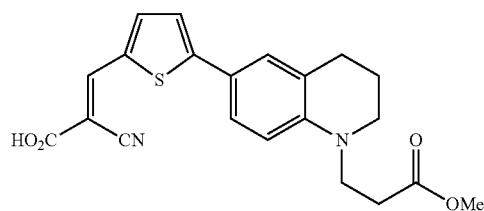 [SMILES: COC(=O)CCN1CCCc2cc(-c3ccc(/C=C(\C#N)C(=O)O)s3)ccc21]

To a 10 ml round bottle flask, 6 (29.1 mg, 0.066 mmol), $K_2CO_3$ (45.6 mg, 0.33 mmol), and DMF (1.32 ml) were added. After stirring for 20 min, methyl iodide (4.1 μl, 0.066 mmol) was added to the reaction and the reaction was stirred at 40° C. for 24 hours. The desired compound was purified using column chromatography (5% MeOH in $CHCl_3$, v/v). The solvent was then removed in vacuo to give deep red powder (20.9 mg, 0.046 mmol, 70% yield). The purified material was dissolved in DCM/TFA mixture in 2:1 ratio and stirred for 1 hour at room temperature. The solvent was then removed in vacuo and the compound was purified using HPLC (50-90% MeCN/$H_2O$ over 10 min, 0.1% TFA, rt=8.5 min.) The solvent was removed in vacuo (17.3 mg, 0.044 mmol, 95% yield). $^1H$ NMR (500 MHz, Chloroform-d) δ 8.15 (s, 1H), 7.63 (d, J=4.1 Hz, 1H), 7.42 (dd, J=8.6, 2.4 Hz, 1H), 7.32-7.29 (m, 1H), 7.21 (d, J=4.1 Hz, 1H), 6.59 (d, J=8.7 Hz, 1H), 3.70 (s, 3H), 3.67 (t, J=7.2 Hz, 2H), 3.40-3.32 (m, 2H), 2.79 (t, J=6.3 Hz, 2H), 2.63 (t, J=7.2 Hz, 2H), 2.00-1.92 (m, 2H); TOF-HRMS (ES+) m/z (M+1) calculated for 453.1848, found: 453.1847.

(E)-N⁶-(3-(5-(1-(2-carboxyethyl)-1,2,3,4-tetrahydro-quinolin-6-yl)thiophen-2-yl)-2-cyanoacryloyl)-L-lysine (Rf490)

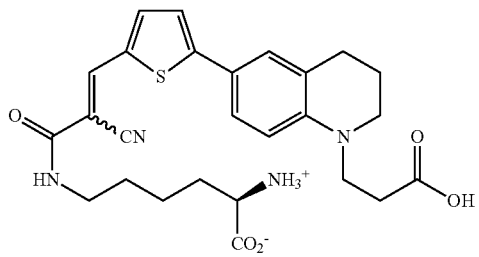

The cyano-acrylate ethyl ester derivative (17.3 mg, 0.044 mmol, 7) was dissolved in 1 mL DMF and purged with Argon gas. After 15 minutes, TSTU (27 mg, 0.088 mmol) and DIEA (0.024 ml, 0.132 mmol) were added and the reaction was stirred for 2.5 hours at room temperature. TSTU activation was monitored by HPLC and mass spectrometry. After starting material was completely consumed, Boc-D-lysine (22.2 mg, 0.088 mmol) was added to the reaction. This was stirred overnight at room temperature. The solution was then diluted with EtOAc (15 mL), followed by washing with 1M HCl (10 mL) twice, brine (10 mL) once, dried over MgSO₄ and then concentrated in vacuo. The crude residue was dissolved in DCM/TFA mixture in 2:1 ratio and stirred for 2 hours at room temperature. After removing the solvent in vacuo, the resulting free acid derivative was dissolved in THF/H₂O mixture (1:1, 2 ml for each). Once the starting material was fully dissolved, LiOH was added (5.3 mg, 0.22 mmol). This reaction was stirred for 1 hour at 40° C., followed by neutralization using 1M HCl. After removing the solvent in vacuo, the crude product was purified by preparative HPLC. The fractions containing the product were lyophilized to provide Rf490·TFA salt (5.5 mg, 0.009 mmol, 20% yield). ¹H NMR TOF-HRMS (ES+) m/z (M+1) Calculated for 511.2015, found: 511.2011.

UV-Vis Spectra and Calibration Curve of FMR-DAAs

The excitation and emission wavelengths of FMR-DAAs were measured by SpectraMax M2 plate reader using disposable cuvette (polymethyl methacrylate). UV-Vis spectra of FMR-DAAs were measured by scanning within a range from 350 to 800 nm with an increment of 1 nm. The wavelength at maximum absorbance (Ex) and emission (Em) of FMR-DAAs were recorded.

For plotting calibration curves, FMR-DAAs (100 mM stock solution, DMSO) were diluted into 1×PBS (pH 7.4) and the corresponding A. absorbance of FMR-DAAs was measured as a function of concentration (0.1, 0.05, 0.025 and 0.0125 mM). The absorptivity was calculated as described by Beer's Law. The spectra of molecular rotor designs are illustrated in FIG. 7 (panels (i)-(vi)).

Measurement of Solubility (Log $D_{7.4}$) of FMR-DAAs

FMR-DAAs (100 mM stock solution, DMSO) were diluted with 2 ml 1×PBS (NaCl 8 g/L, KCl 0.2 g/L, Na2HPO4-2H2O 1.78 g/L, KH2PO4 0.27 g/L, pH 7.4) to a final concentration of 0.05 mM. The FMR-DAAs solution was extracted with 2 ml 1-octanol once. The absorbance of the PBS layer was measured (SpectraMax M2 plate reader, disposable cuvette) to calculate the amount of remained FMR-DAAs in PBS layer using the calibration curves. The Log D7.4 value was calculated by the following equation (Lombardo el al, *J Med Chem*, 2001, 44, 2490).

$$\text{Log} D_{PBS,pH7.4} = \text{Log} \frac{[Solute]_{1-octanol}}{[Solute]_{PBS,pH7.4}}$$

Measurement of Thermal Stability of FMR-DAAs

FMR-DAAs (100 mM stock solution, DMSO) was diluted with 1×PBS (pH7.4) to a final concentration of 0.05 mM. The FMR-DAAs solution was then incubated at 60° C. and kept from light exposure. The absorbance was measured after 8 hours incubation (SpectraMax M2 plate reader, disposable cuvette) and the amount of remained FMR-DAAs was calculated by using the calibration curves mentioned above. The stability was described as the ratio of the FMR-DAAs concentration at $8^{th}$ hour to the original concentration.

Culture Growth.

Strain characteristics and growth conditions are shown in Table 1. Bacterial cells were inoculated from −80° C. frozen tubes onto LB agar plates and incubated overnight at 37° C. for *Bacillus subtilis* and *Escherichia co*, or 30° C. for *Streptomyces venezuelae*. Cells from single colonies were transferred to liquid LB medium and incubated in an Innova® 44R shaker at 37° C. or 30° C. After the cell cultures reached $OD_{600}$ ~0.5, they were diluted with LB medium to $OD_{600}$ ~0.05 (10×) and again incubated in the shaker until $OD_{600}$ ~0.5. The cells were then used for labeling experiments.

TABLE 1

Bacterial Strains

| Species | Background | Source | # | Gram | Growth temperature |
|---|---|---|---|---|---|
| *Bacillus subtilis* (WT) | 3610 | Brun Lab (IU) | YB7447 | + | 37 |
| *Escherichia coli* (WT) | BW25113 | Brun Lab (IU) | YB7421 | − | 37 |
| *Escherichia coli* imp4213 | BW25113 | Huang Lab (Stanford) | KC440 | − | 37 |
| *Streptomyces venezuelae* (WT) | | Brun Lab (IU) | YB6837 | + | 30 |

Rotor/standard Fluorescent D-amino acid labeling. The TFA salts of FMR-DAAs were used for labeling experiments. FMR-DAA/FDAA stock solutions were prepared in DMSO at a concentration of 100 mM and stored at −20° C. before use. For long-pulse labeling of *B. subtilis* and *E. coli*, exponential phase cultures were diluted with fresh LB broth containing 1 mM FDAA to $OD_{600}$ ~0.5 and incubated for 1 h. The cells were then imaged immediately using a Nikon Ti-E inverted microscopy system without washing and fixation. For short-pulse labeling of *S. venezuelae*, FDAA stock solution was added directly to exponential phase cultures to a final concentration of 0.5 mM, followed by incubating at 30° C. with shaking for 15 min. The cells were then imaged immediately. For washed samples, FDAA-labeled cells were collected by centrifugation (7000 g, 1 min) and then resuspended in 37° C. fresh LB broth. This process was repeated twice and the washed cells were resuspended in LB broth before imaging. For time-lapse experiments with unwashed cells, exponentially growing cells were directly used for imaging.

Measurement of Viscosity Sensitivity of FMR-DAAs and FMR-DAAs-Labeled *B. subtilis*

For free FMR-DAAs measurement, FMR-DAAs (100 mM stock solution, DMSO) was diluted in PBS-glycerol solution (1×PBS containing 0%, 20%, 40%, 50%, 60% and 80% glycerol, pH 7.4) to a final concentration of 0.1 mM. The solutions were transferred into 96-well micro-plate and the fluorescence was measure at corresponding Em wavelength mentioned above using SpectraMax M2 plate reader (corresponding Ex wavelength was used). The viscosity sensitivity was calculated using the following equation, where r is viscosity of the solvents, I is the emission intensity of the FMR-DAAs, C is a constant depending on the temperature, and x is the viscosity sensitivity (Zhou el, *EJOC*, 2011, 4773). The $I_{g, 50\%}/I_w$ value represents the ratio of fluorescent intensity of the 50% glycerol sample to that of the 0% glycerol sample.

For FMR-DAAs-labeled *B. subtilis*, long-pulse labeled cells were first prepared as mentioned above. The cells were centrifuged and fixed with ice-cold ethanol (70%) for 30 minutes. The fixed cells were washed with 1×PBS (pH 7.4) twice and resuspended in PBS-glycerol solution (1×PBS containing 0%, 20%, 40%, 50%, 60% and 80% glycerol, pH 7.4). The viscosity sensitivity was measured and calculated as described above. Tables 2 provide physical property data for the molecular rotor designs.

cells were loaded onto 1.5 mm coverslip, covered with PBS-agarose pad (1.5% w/v) and immediately imaged by Nikon 90i fluorescence microscope without washing steps. FIG. 8 illustrates the results of labeling the *Streptomysis venezuulae* cells with first generation and third-sixth generation molecular rotor designs (panels (i)-(v)).

Long-Pulse Labeling of *B. subtilis*, *E. Coli* and *A. tumefaciens* with FMR-DAAs Cells in exponentially growing state (OD≈0.2) were incubated in LB broth culture medium ($S7_{50}$ medium was used for *A. tumefaciens*) containing 0.5 mM FMR-DAA (0.5% DMASO) for 60 minutes at 37° C. (*B. subtilis* wt, *B. subtilis* ΔdacA, *E. coli* wt and *E. coli* imp) or 240 minutes 26° C. (*A. tumefaciens*). The cells were loaded onto 1.5 mm coverslip, covered with PBS-agarose pad (1.5% w/v) and imaged by Nikon 90i fluorescence microscope without washing steps. FIG. 9 illustrates the results of labeling *B. subtilis*, *E. coli* and *A. tumefaciens* cells with first generation and third-sixth generation molecular rotor designs (panel sets (i)-(v)).

Time-Lapse Labeling of *S. venezuelae* and *B. subtilis* with FMR-DAAs (Rotor No. 4)

Cells in exponentially growing state (OD≈0.2) were loaded onto 1.5 mm coverslip and covered with LB-agarose pad (1.5% w/v) containing FMR-DAA (Rotor No. 4, 0.5 mM). A metal ring with transparent cap was used to cover the sample to prevent the sample from evaporation. The cells were imaged with intervals of 3 minutes (*B. subtilis* wt, 37° C.) or 5 minutes (*S. venezuelae*, 30° C.) using a Nikon Ti-E inverted fluorescence microscope. (470 nm excitation and Cy3 emission filter were used.) FIG. 10 illustrates the results of labeling *S. venezuelae* and *B. subtilis* cells with fourth generation molecular rotor design overtime (0-35 min).

Sacculi Purification of *B. subtilis* ΔdacA Labeled with FMR-DAA (Rotor No. 4)

TABLE 2

Photochemical and physical properties of Rf420, Rf470, Rf490 and HADA

| | Rf420 | Rf470 | Rf490 | HADA |
| --- | --- | --- | --- | --- |
| MW (unsalted) | 428.5 | 510.6 | 510.6 | 292.1 |
| Max. $\lambda_{Ex}$ [a] | 420 | 470 | 490 | 400 |
| Max. $\lambda_{Em}$ [a] | 490 | 640 | 660 | 450 |
| Viscosity sensitivity ($\chi$) | 0.683 ± 0.013 | 0.642 ± 0.022 | 0.67 ± 0.003 | 0.025 ± 0.003 |
| Quantum Yield ($\phi$) [a, b] | 0.012 | 0.042 | 0.035 | NA |
| Absorptivity ($\epsilon$) [c] | 19761 | 33106 | 25409 | 109538 |
| Water-solubility (Log $D_{7.4}$) [d] | −1.497 ± 0.045 | −1.150 ± 0.09 | −1.10 ± 0.07 | −1.059 ± 0.076 |
| Thermo-stability [c, e] | 99.8 ± 1.2% | 99.4 ± 1.4% | 96.9 ± 9.8% | 80.0 ± 1.1% |

[a] Data were measured in PBS (pH 7.4) containing 50% glycerol
[b] Fluorescein was used as standard for quantum yield measurements.
[c] Data were measured in PBS (pH 7.4).
[d] Data were measure in 1X PBS (pH 7.4) and 1-octanol extraction. A smaller value represents greater water solubility.
[e] Value represents signal retention of absorbance after a 24-hours incubation at 60° C. compared to the corresponding initial value.

Fluorescence Microscopy Imaging

Phase and fluorescence microscopy was performed with a Nikon 90i fluorescence microscope equipped with a Plan Apo 100×/1.40 Oil Ph3 DM objective and a Chroma 83700 triple filter cube with corresponding excitation and emission filters. All images were captured using NIS software from Nikon and a Photometrics Cascade 1K cooled charge-coupled device camera, and were processed and analyzed using ImageJ.

Short-Pulse Labeling of *Streptomysis venezuunlae* with FMR-DAAs

Cells in exponentially growing state (OD≈0.2) were incubated in LB broth culture medium containing 0.5 mM FMR-DAA (0.5% DMSO) for 10-15 minutes at 30° C. The Exponentially growing cells were incubated in LB broth culture medium containing FMR-DAA (Rotor No. 4, 0.5 mM, 0.5% DMSO) for 60 minutes at 37° C. The cells were collected, washed once with 1×PBS and fixed with ice-cold methanol (70%) for 30 minutes. Fixed cell was centrifuged and washed with 1×PBS (pH 7.4) twice and 1×PBS-SDS solution (0.5% SDS, pH 7.8) once. The cell was incubated in 1×PBS-SDS solution containing 1.5 mg/ml pronase E (Sigma-Aldrich, *Streptomyces griseus*) for 2 hours at 60° C. The cell was collected, washed with $H_2O$ once, resuspended in 4% SDS-$H_2O$ solution and boiled for 1 hour. The boiled pellets were washed with $H_2O$ twice and imaged by Nikon 90i fluorescence microscope. FIG. 11 illustrates the results of labeling *B. subtilis* cells with HADA (panel set (i)), D-form of fourth generation molecular rotor design (panel set (ii)) and L-form of fourth generation molecular rotor design (panel set (iii)).

INCORPORATION BY REFERENCE

All of the patents, patent applications, patent application publications, other publications and appendices cited herein are hereby incorporated by reference as if set forth in their entirety.

Preferred Embodiments

The present invention has been described in connection with what are presently considered to be the most practical and preferred embodiments. However, the invention has been presented by way of illustration and is not intended to be limited to the disclosed embodiments. Accordingly, one of skill in the art will realize that the invention is intended to encompass all modifications and alternative arrangements within the spirit and scope of the invention as set forth in the appended claims.

The invention claimed is:
1. A modified amino acid comprising a D-amino acid covalently attached to either structure (I) or structure (II):

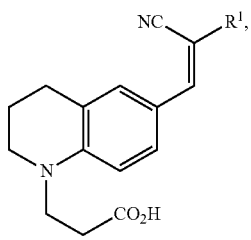
(I)

wherein R' is selected from —CN and —$CO_2H$; and

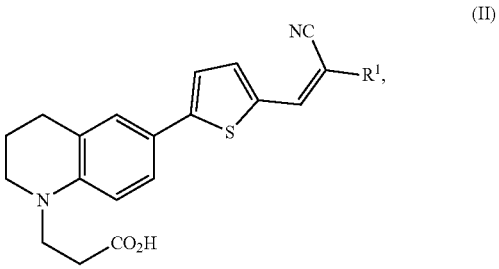
(II)

wherein R' is selected from —CN, —$CO_2H$ and $SO_3H$.

* * * * *